(12) United States Patent
Roland et al.

(10) Patent No.: US 11,564,981 B2
(45) Date of Patent: Jan. 31, 2023

(54) VACCINE FOR PREVENTION OF NECROTIC ENTERITIS IN POULTRY

(71) Applicant: ARIZONA BOARD OF REGENTS ON BEHALF OF ARIZONA STATE UNIVERSITY, Scottsdale, AZ (US)

(72) Inventors: Kenneth Roland, Mesa, AZ (US); Andrew Diamos, Mesa, AZ (US); Hugh Mason, Phoenix, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 17/474,797

(22) Filed: Sep. 14, 2021

(65) Prior Publication Data
US 2021/0401962 A1 Dec. 30, 2021

Related U.S. Application Data

(62) Division of application No. 16/628,860, filed as application No. PCT/US2018/040632 on Jul. 2, 2018, now Pat. No. 11,154,606.

(60) Provisional application No. 62/528,696, filed on Jul. 5, 2017.

(51) Int. Cl.
| | | |
|---|---|---|
| A61K 39/08 | (2006.01) | |
| A61P 31/04 | (2006.01) | |
| C12N 15/74 | (2006.01) | |
| C12N 15/82 | (2006.01) | |
| A61K 39/00 | (2006.01) | |

(52) U.S. Cl.
CPC ............ *A61K 39/08* (2013.01); *A61P 31/04* (2018.01); *C12N 15/74* (2013.01); *C12N 15/8258* (2013.01); *A61K 2039/552* (2013.01); *A61K 2039/55577* (2013.01)

(58) Field of Classification Search
None
See application file for complete search history.

*Primary Examiner* — Oluwatosin A Ogunbiyi
(74) *Attorney, Agent, or Firm* — Viksnins Harris Padys Malen LLP

(57) ABSTRACT

In certain embodiments, the present invention provides a poultry vaccine comprising an antigenic protein comprising a PlcC protein unit that is operably linked to a peptide linker that is operably linked to a NetB protein unit, where

VACCINE FOR PREVENTION OF NECROTIC ENTERITIS IN POULTRY

CROSS-REFERENCE TO RELATED APPLICATIONS

This application is a divisional application of U.S. patent application Ser. No. 16/628,860, filed Jan. 6, 2020, now U.S. Pat. No. 11,154,606 published Oct. 26, 2021, which claims priority to International Application Number PCT/US2018/040632, filed Jul. 2, 2018, which claims the benefit of priority of U.S. Provisional Application Ser. No. 62/528,696, filed Jul. 5, 2017. The entire content of the applications referenced above is hereby incorporated by reference herein.

SEQUENCE LISTING

The instant application contains a Sequence Listing which has been submitted in ASCII format via EFS-Web and is hereby incorporated by reference in its entirety. Said ASCII copy, created on Aug. 10, 2018 is named 17555_051WO1_SL.txt and is 45,056 bytes in size.

BACKGROUND

*C. perfringens* is a ubiquitous gram positive, spore-forming, anaerobic organism, found in many environments surrounding poultry production, including soil, dust, feces, feed, litter, rodents, and the intestinal contents of asymptomatic animals. *C. perfringens* is classified into five groups based on the types of toxins secreted, but only *C. perfringens* type A strains are commonly associated with enteric disease in poultry. The toxins produced by type A *C. perfringens* strains cause necrotic enteritis (NE) in colonized birds. Severe acute cases can result in sudden death, while subclinical necrotic enteritis results in thickening of the intestinal mucosa and decreased length of microvilli in the ileum. The collective impact of *C. perfringens* colonization is to reduce the absorptive surface in the intestinal tract with a consequent reduction in the ability of birds to benefit from nutrients in food, resulting in a reduced rate of growth. *C. perfringens* also induces cellulitis and gangrenous dermatitis and is becoming an increasing concern in turkeys as well.

This application claims the benefit of priority of U.S. Provisional Application Ser. No. 62/528,696, filed Jul. 5, 2017, which application is incorporated by reference herein.

*C. perfringens* infections and NE have been traditionally controlled by addition of Antimicrobial Growth Promoters (AGP) and coccidiostats in the animal feed. Large quantities of antimicrobials were used as AGP and as prophylaxis against enteric bacterial pathogens, including *C. perfringens*. The use of AGP has been condemned due to concerns about increased antibiotic resistance in human pathogens. Consequently, an increase in the incidence of sub-clinical NE is linked to the withdrawal of AGP. This had been observed initially in Scandinavian countries following the ban on AGP in the early 1990s. Furthermore, the decline in use of ionophore coccidiostats, which can prevent *C. perfringens* lesions, has exacerbated the resurgence of NE. Recent moves by the US congress and the FDA to restrict the use of growth promoting antibiotics and public pledges by major poultry consumers (e.g. McDonald's, Costco, Chick-fil-A) to eliminate antibiotic-fed poultry from their menus, indicates that the old practices are on the way out. Thus, NE is a re-emerging disease and a threat to the current objective of "antimicrobial-free" poultry farming.

Most birds infected with virulent strains remain asymptomatic and show reduced growth performance. *C. perfringens* can cause a range of health problems in infected birds, ranging from a subclinical infection which can result in poor feed conversion caused by decreased digestion and adsorption, to necrotic enteritis, resulting in a variety of symptoms including severe depression, decreased appetite, reluctance to move, diarrhea and ruffled feathers, often leading to death. Clinical illness is usually short, with birds often simply found dead. Onset of disease symptoms generally occurs in broilers from two to five weeks of age, coinciding with the disappearance of maternal antibodies. However, NE has also been reported in layers of various ages. Gross lesions typically involve the duodenum, jejunum and sometimes the ileum, although even cecal lesions can occur. Intestines are friable and distended with gas and fluid and a diphtheritic membrane is often found in the mucosa. Subclinical infection with *C. perfringens* can lead to economic losses, due to reduced growth rates and poor feed conversion. It is likely that losses due to subclinical infections may constitute a larger problem overall than losses due to acute disease. Occasionally, cholangiohepatitis can result, leading to condemnation losses.

Diet has also been implicated as a factor that can predispose birds to NE. Inclusion of wheat, rye, barley, oat groats or fish meal in the diet can lead to increased numbers of *C. perfringens* and incidence of NE. Dietary fat source can also influence the *C. perfringens* population (19). Current thinking is that predisposing factors such as a high protein diet (e.g. fishmeal) and/or *Eimeria* infection result in alterations of the chicken gut microbiota that allow incoming pathogenic *C. perfringens* strains to become established.

Thus, there is an unmet need for an improved, effective vaccine against *C. perfringens* that protects the birds against the disease. A vaccine that would protective immunity would meet this need.

SUMMARY

Necrotic enteritis caused by *Clostridium perfringens* is a serious economic problem in the broiler industry, with losses up to $2 billion annually. In the US, this problem is likely to be exacerbated as the use of antibiotics in poultry rearing is phased out. This invention describes a method to produce in plants, a novel protein fusing two toxoids that elicit immune responses protective against necrotic enteritis. The fusion protein antigen can be purified from plant cells for use as an injectable vaccine or can by directly applied to poultry feed for use as an oral vaccine.

In certain embodiments, the present invention provides an antigenic protein comprising a PlcC protein unit that is operably linked to a peptide linker that is operably linked to a NetB protein unit.

In certain embodiments, the present invention provides a nucleic acid encoding the antigenic protein described herein.

In certain embodiments, the present invention provides an expression cassette comprising the nucleic acid described herein and a promoter.

In certain embodiments, the present invention provides a recombinant vector comprising the expression cassette described herein and a vector.

In certain embodiments, the present invention provides a plant cell comprising the antigenic protein described herein, the nucleic acid described herein, the expression cassette described herein or the recombinant vector described herein.

In certain embodiments, the present invention provides animal feed comprising the plant cell described herein.

In certain embodiments, the present invention provides a vaccine comprising the antigenic protein described herein, the nucleic acid described herein, the expression cassette described herein, the recombinant vector described herein, the plant cell described herein, or the animal feed described herein.

In certain embodiments, the present invention provides a method of protecting an avian species from *C. perfringens* infections comprising administering the vaccine described herein.

Figure 1:
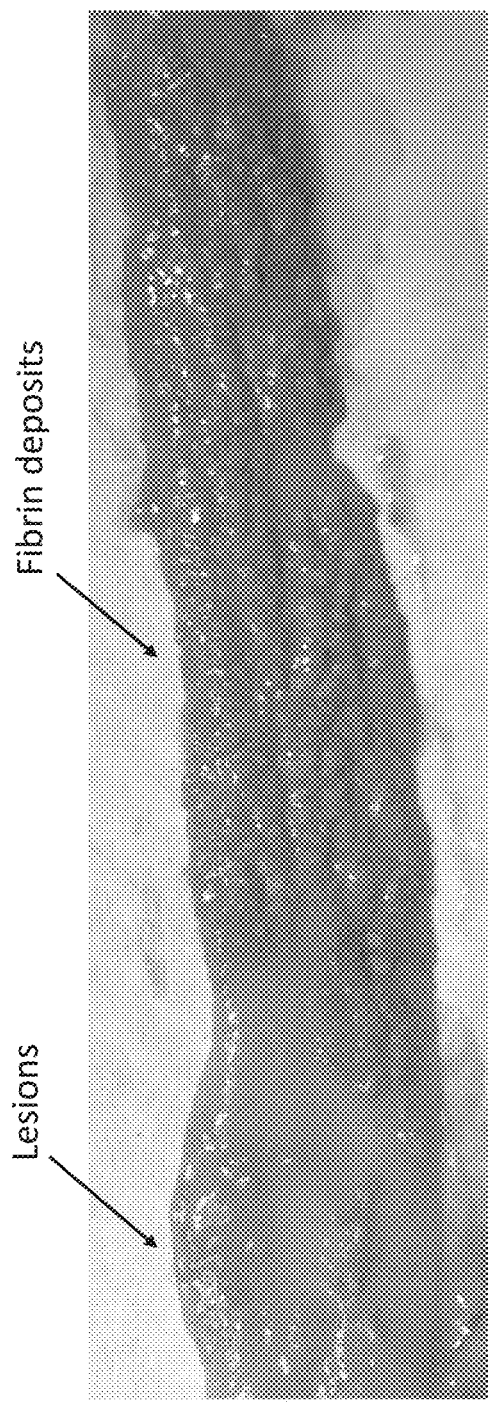
FIG. 1. Fibrin deposits and lesions on the intestinal tract of a chicken with necrotic enteritis.

FIG. 2. Schematic of PlcC-NetB fusion protein.

FIG. 3. Western blot of plant-made PlcC-NetB fusion and NetB proteins. Extracts of *N. benthamiana* leaf samples expressing either PlcC-NetB fusion or NetB proteins were resolved by SDS-PAGE and electro-blotted to a PVDF membrane and probed with rabbit anti-NetB serum. For NetB, 4 different forms can be observed, with the smallest at ~34 kDa (the theoretical size of unglycosylated NetB) and the largest ~46 kDa, suggesting glycosylation at all 4 potential Asn-linked sites. For PlcC-NetB fusion protein, the theoretical size of unglycosylated protein is ~49 kDa; the observed bands occur between ~52 kDa and 62 kDa, with the largest suggesting glycosylation at all 5 potential Asn-linked sites.

FIGS. 4A-4C. IgY serum titers from immunized and non-immunized birds in Experiment 1. A paired t-test was performed between chickens that received the fusion protein and non-vaccinated control group. FIG. 4A. PlcC0NetB titers; FIG. 4B. PlcC titers; FIG. 4C. NetB titers. * $P \leq 0.009$.

FIG. 5. Summary of lesion scores from Experiments 1 and 2.

FIG. 6. Map of pBYR2eK2M-6HplcCnetB.

DETAILED DESCRIPTION

Necrotic enteritis (NE) is caused by type A strains of the bacterium *Clostridium perfringens*. The total global economic losses to the poultry industry due to NE is estimated to be over 2 billion dollars annually. *C. perfringens* produces two toxins, alpha-toxin and NetB. The NetB toxin is responsible for the symptoms associated with NE and anti-NetB antibodies are protective. Immune responses against alpha-toxin are partially protective despite the fact that it does not play a direct role in NE. We describe a single fusion protein combining immunogenic and non-toxic components of alpha-toxin and NetB that can be used to immunize poultry against NE. The fusion protein is produced in plants which can be purified and used as an injectable preparation or fed directly to poultry to elicit a protective immune response.

The use of plants for the production and oral delivery of a necrotic enteritis vaccine is novel. Moreover, the PlcC-NetB fusion protein described here is novel and is strongly expressed in plants, which lack cholesterol and thus may be immune to the toxic effects of NetB, thus permitting the observed high expression level.

This novel fusion protein combines the two most potent protective antigens against necrotic enteritis, NetB and alpha-toxin, into a single antigenic protein. NetB is the toxin responsible for necrotic enteritis symptoms. The alpha-toxin (Plc) may also contribute to disease, and, in addition, antibodies against alpha-toxin are targeted to the surface of *C. perfringens*, inhibiting its growth. However, strains lacking alpha-toxin can cause disease, such that a vaccine relying only on immune responses against alpha-toxin will not provide protection against these strains. Combining both alpha-toxin and NetB epitopes will provide robust protection against disease. The PlcC-NetB protein can be purified from plants, in either a glycosylated or non-glycosylated form, and used as an injectable vaccine to protect birds directly. Injection into hens will protect their offspring in the first two weeks of life via maternal antibodies passed on in the egg. When this protein is produced in a food plant, such as corn, with or without an LT adjuvant, the resulting recombinant plant can be applied directly to the feed, resulting in a potentially low cost, oral vaccine to protect chickens against necrotic enteritis.

The use of plants for the production and oral delivery of a necrotic enteritis vaccine is novel. Moreover, the PlcC-NetB fusion protein described here is novel and is strongly expressed in plants, which lack cholesterol and thus may be immune to the toxic effects of NetB, thus permitting the observed high expression level.

*C. perfringens* type A strains produce alpha-toxin, a membrane-damaging phospholipase C enzyme. The toxin is hemolytic, necrotizing and lethal. It is the toxin that responsible for *C. perfringens*-mediated gas gangrene. Many of the symptoms of NE can be reproduced with culture-free supernatants of *C. perfringens*. Since these supernatants were known to contain alpha-toxin, it was assumed that alpha-toxin was responsible. More recent studies have identified a novel toxin linked to necrotic enteritis, designated NetB toxin. It was first identified in a virulent *C. perfringens* type A strain isolated in Australia and it has been detected in the vast majority of NE-associated *C. perfringens* strains throughout the world. Thus, it is now considered to be the most critical virulence factor for the development of NE in broilers. NetB is a pore-forming toxin encoded on a large conjugative plasmid (approximately 85 kb) within a 42 kilobase (kb) pathogenicity locus (NELoc-1), showing similarity to *C. perfringens* β-toxin (38% identity). The presence of netB gene is highly correlated with necrotic enteritis strains. NetB is also a protective antigen, particularly in combination with other immunogenic components. One study showed that the levels of serum antibodies against both alpha-toxin and NetB toxin were significantly higher in apparently healthy chickens compared to birds with clinical signs of NE, suggesting that these antitoxin antibodies play a role in protection. The large clostridial cytotoxin TpeL (predicted molecular mass=191 kDa), first identified in type C strains, is also produced by some type A strains and has been linked to increased virulence, particularly in strains producing netB. However, it should be noted that a recent study of historical NE strains collected >15 years ago in Alabama revealed a low prevalence of the netB gene, indicating that netB may be dispensable for some NE for some strains or in some situations. Nevertheless, it is clear that the overwhelming majority of current necrotic enteritis strains produce this toxin.

Toxins have traditionally been targeted as antigens of interest for controlling clostridial infections. The *C. perfringens* alpha-toxin (Plc) is the major virulence determinant for gas gangrene and antibodies to *C. perfringens* alpha-toxin prevent gas gangrene in mice. The *C. perfringens* gene encoding alpha-toxin is plc (for phospholipase C). The protein is divided into two domains, the amino-terminal domain encodes the catalytic site responsible for phospholipase activity, while the carboxy-terminal domain is involved in interactions with phospholipids, targeting the enzyme to host cell membranes. The alpha-toxin carboxy-terminal fragment (amino acids 247-370) is non-toxic and immunization with this fragment confers protection against alpha-toxin and *C. perfringens* in a gas gangrene mouse model. Immune responses against the C-terminal domain, PlcC, can provide protection against subsequent challenge with *C. perfringens*.

NetB binds to cholesterol in membranes, forming heptameric pores. A number of single amino acid substitutions in the rim loop region can significantly reduce its ability to bind to cells and its toxicity. These include Y191A, R200A, W257A and W262A, S254L, R230Q and W287R. Some of these were shown to retain the ability to generate protective immune responses, including W262A and S254L. A number of studies have demonstrated the potential of vaccination to control NE. A vaccine utilizing detoxified alpha-toxin can induce some protection against experimental infection. Since alpha-toxin is not required in order for *C. perfringens* to cause NE in chickens, it is not clear why alpha-toxoids are protective. One likely explanation is based on data showing that anti-alpha-toxin (anti-Plc) antibodies bind to the surface of Plc+*C. perfringens* strains and that these antibodies can also inhibit *C. perfringens* growth. Thus, it is possible that the reason anti-Plc antibodies are protective is due to their growth inhibitory properties and not directly due to detoxification.

NetB is also a protective antigen, which could provide significant protection against NE challenge, especially in combination with other immunogenic components. Both alpha-toxin (C-fragment) and NetB (W262A) toxoids were combined (30 g of each) in Quil A adjuvant and used to subcutaneously inject broiler birds 3 times, on days 3, 9 and 15. Birds injected with only one of the proteins were also included. The immunized birds were partially protected against a mild challenge (gavage only), but not against a more severe, in feed challenge. In some studies, hens were infected with NetB toxoid and antibodies against NetB were transferred from immunized hens to their progeny, providing protection to the chicks against *C. perfringens* challenge. In another study, immunization with both NetB and alpha-toxin toxoids using a live *Salmonella* delivery vector induced mucosal antibodies against both toxins and elicited a protective response. S. *Typhimurium* vaccine trains engineered to deliver both toxoids provided significantly better protection than strains delivering each toxin alone.

Recently an injectable alpha-toxoid preparation produced by Intervet, called Netvax, has come on the market for use in broiler breeders to increase protection in chicks during the first few weeks of life. However, there is no commercial vaccine that includes a NetB immunogenic component. Several vaccine antigens have been stably expressed in corn and rice, which are convenient for use in feed products. Despite concerns regarding oral tolerance, feeding animals plant-based vaccines has been shown to be effective in agricultural animals, including poultry.

Proteins

In certain embodiments, the present invention provides an antigenic protein comprising a PlcC protein unit that is operably linked to a peptide linker that is operably linked to a NetB protein unit.

In certain embodiments, the PlcC protein unit, the peptide linker and the NetB protein unit each have an N-terminus and a C-terminus, and wherein the C-terminus of the PlcC protein unit is linked to the N-terminus of the peptide linker, and the C-terminus of the peptide linker is operably linked to the N-terminus of the NetB protein unit.

In certain embodiments, the PlcC protein unit has at least 95% sequence identity to SEQ ID NO: 3. The PlcC protein unit of SEQ ID NO: 3 is amino acids 248-370 of alpha toxin (GenBank accession AAP-15462.1).

In certain embodiments, the PlcC protein unit has 100% sequence identity to SEQ ID NO: 3.

In certain embodiments, the NetB protein unit has at least 95% sequence identity to SEQ ID NO: 5. The NetB protein unit of SEQ ID NO: 5 is amino acids 31-322 of (GenBank accession ACN73257.1).

In certain embodiments, the NetB protein unit has one or more amino acid substitutions at Y191A, R200A, W257A and W262A, S254L, R230Q or W287R of SEQ ID NO: 5.

In certain embodiments, the NetB protein unit has 100% sequence identity to SEQ ID NO: 5.

In certain embodiments, the peptide linker has at least 95% sequence identity to SEQ ID NO: 4.

In certain embodiments, the peptide linker has 100% sequence identity to SEQ ID NO: 4.

In certain embodiments, the antigenic protein further comprises a 6Hist tag having an N-terminus and a C-terminus, wherein the C-terminus of the 6Hist tag is operably linked to the N-terminus of the PlcC protein unit.

In certain embodiments, the 6His tag has 100% identity to SEQ ID NO: 2.

In certain embodiments, the antigenic protein further comprises a plant signal peptide having an N-terminus and a C-terminus, wherein the C-terminus of the plant signal peptide is operably linked to the N-terminus of the 6Hist tag.

In certain embodiments, the plant signal peptide has at least 95% sequence identity to SEQ ID NO: 1.

In certain embodiments, the plant signal peptide has 100% sequence identity to SEQ ID NO: 1.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes peptides with reduced peptide bonds, which will prevent proteolytic degradation of the peptide. Also, the term includes the amino acid analog α-amino-isobutyric acid. The term also includes natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

A "variant" of one of the proteins that one that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Aline is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 80%, at least about 90%, or even at least about 91%, 92%, 93%, 94%, 95%, 96%, 97%, 98%, 99%, but less than 100%, contiguous amino acid sequence homology or identity to the amino acid sequence of a corresponding native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The terms "protein," "peptide" and "polypeptide" are used interchangeably herein.

Amino acid sequence of 6H-plcC-netB fusion protein:

```
                                              (SEQ ID NO: 13)
mankhlslslflyllglsaslasgHHHHHHgsDPSVGNNVKELVAYISTS

GEKDAGTDDYMYFGIKTKDGKTQEWEMDNPGNDFMAGSKDTYTFKLKDEN

LKIDDIQNMWIRKRKYTAFPDAYKPENIKVIANGKVVVDKDINEWISGNS

TYNIKggsggsggpsggsggsELNDINKIELKNLSGEIIKENGKEAIKYT

SSDTASHKGWKATLSGTFIEDPHSDKKTALLNLEGFIPSDKQIFGSKYYG

KMKWPETYRINVKSADVNNNIKIANSIPKNTIDKKDVSNSIGYSIGGNIS

VEGKTAGAGINASYNVQNTISYEQPDFRTIQRKDDANLASWDIKFVETKD

GYNIDSYHAIYGNQLFMKSRLYNNGDKNFTDDRDLSTLISGGFSPNMALA

LTAPKNAKESVIIVEYQRFDNDYILNWETTQARGTNKLSSTSEYNEFMFK

INWQDHKIEYYL
```

Coding of Regions:

Lower case, regular type=ER signal peptide from barley alpha amylase gene

Upper case, Italics=6-His metal affinity tag

Lower case, italics=linker sequences

Upper case, regular type=plcC

Upper case, Bold type=netB (W262A mutation underlined)

In certain embodiments, e.g., for cytosolic instead of ER targeting, the N-terminal signal peptide (Lower case, regular type) is omitted.

Nucleic Acid

In certain embodiments, the present invention provides a nucleic acid encoding the antigenic protein described herein.

In certain embodiments, the nucleic acid has been plant-codon optimized for plant expression.

In certain embodiments, the nucleic acid has been plant-codon optimized for expression in *Nicotiana benthamiana* or *Arabidopsis.*

In certain embodiments, the nucleic acid has at least 95% sequence identity to SEQ ID NO: 6.

In certain embodiments, the nucleic acid has 100% sequence identity to SEQ ID NO: 6.

The fusion protein gene for the 6H-plcC-netB fusion protein (SEQ ID NO: 13 (amino acid sequence)) was codon optimized for expression in *Nicotiana benthamiana*. Each codon was assessed for its preference of use in highly expressed genes of *N. benthamiana, N. tabacum*, and *Arabidopsis thaliana*, using coding sequences obtained from Genbank accessions (Geyer, B. C., Kannan, L., Cherni, I., Woods, R. R., Soreq, H., and Mor, T. S. (2010) Transgenic plants as a source for the bioscavenging enzyme, human butyrylcholinesterase. Plant Biotechnol J. 8(8):873-86). Use of a particular codon was avoided if it represented less than 50% of the frequency of the most preferred synonymous codon in the reference gene set. The remaining codons were used at frequencies proportional to their frequencies of use in the reference gene set. Furthermore, A-rich sequences that could function as a polyadenylation near-upstream element were avoided, including AATAAA, AATGGA, AATGAA, TATAAA, AATAAT, AATAAG, AATATT, GATAAA, AACCAA, ATATAA, AATCAA, ATACTA, ATAAAA, ATGAAA, AAGCAT, ATTAAT, ATACAT, AAAATA, ATTAAA, AATTAA, AATACA, CATAAA, ACTAAA, and AAAAAA. Sequences that could function as 5' intron splice recognition sequences were avoided, including GTAACA, GTGCTC, GTTAGT, GTAAAT, GTAAAG, GTCTGT, GTAAGG, GTGAGT, GTAAAA, GTAAGT, GTAAGC, GTACGT, GTAACT, GTAAGA, GTTAAA, GTAATA, and GTACAT. As much as possible, sequences that could function as 3' intron splice recognition sequences were avoided, including GCAGG, CCAGG, TCAGG, ATAGG, GTAGG, TTAGG, ACAGG, and AAAGG. Potential RNA destabilizing sequences were avoided, including ATTTA, TAGATY, ATAGAT, and TTTTTT. Potential termination signals for RNA polymerase II were avoided as much as possible, including CA(N7-9)AGTNNA. The potential DNA C-methylation signal CCGG was avoided as much as possible.

Figure 6:
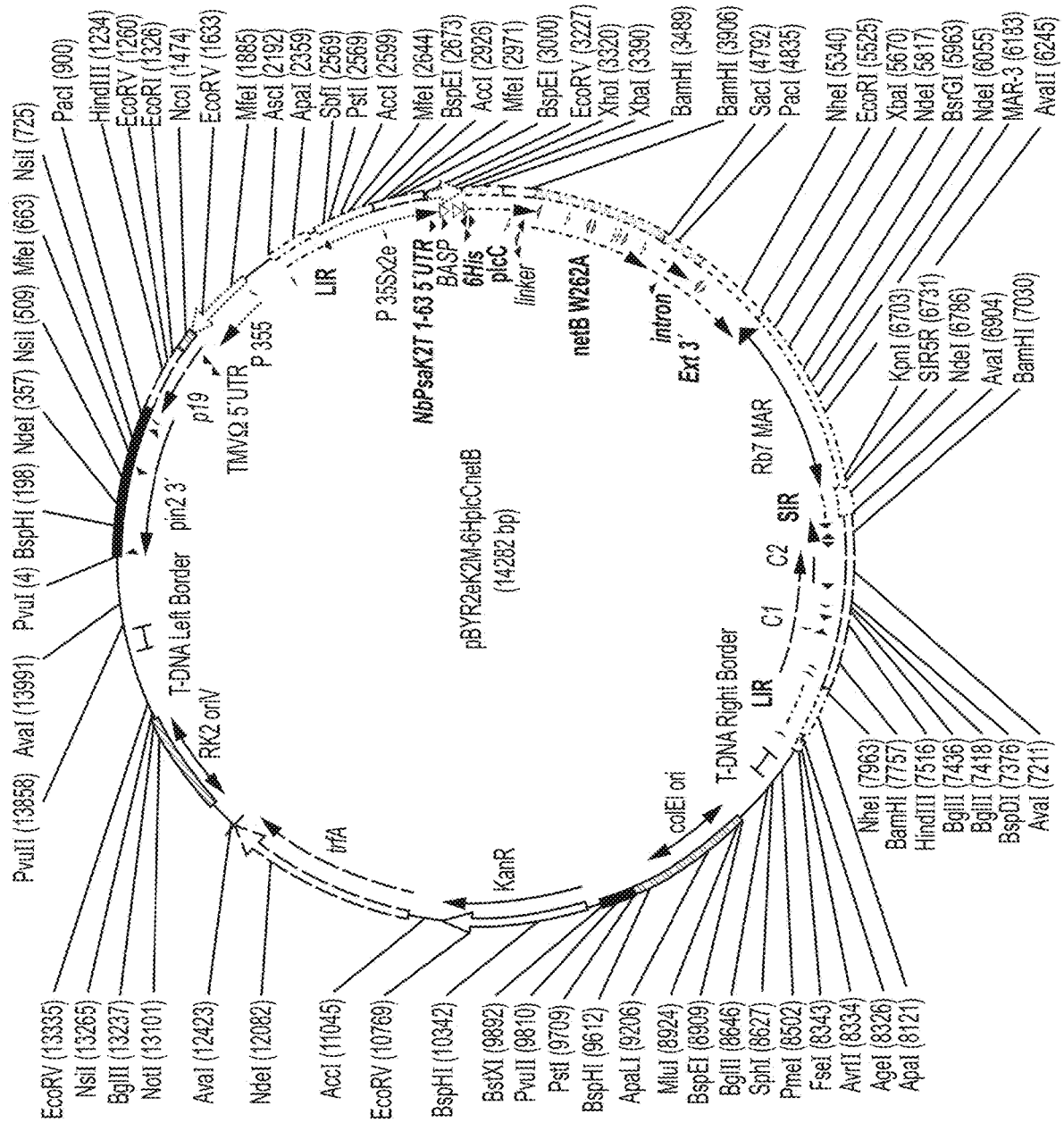

The nucleotide sequence of pBYR2eK2M-6HplcCnetB is the following (FIG. 6):
(SEQ ID NO: 14)

```
CGATCGGTCGATTCATAGAAGATTAGATTTTTCATAGTATTTTTTAAAGTAAACCT

TTAACTACGGTTAGGACACTTTTAAGTTAAATTTAATTTGAACCCTTAAATTAATTTTTAAA

ATAGATAAATATCAATCATCCTGATATGCTTTTGAAAAAATGAATGAGAAAGATGATTCAAT

TAAGGCCACATTTTAATCATGACTAAAATAATATACAGTATAATTTCATATATATTTGCTTT

AAAAAAAAATTGACAATCCATTCGTTTCTAGCAATAAATTTCTTCAACCACAAATATATTAA

AGATAACTACGGCATAGAAACAAAAATCTATGAAGAATTTTTGTATACTTCATATGAAATTA

AAAAAAACTTCATTGAACATCAAAATAATAATAATAATCATAAACTCCTCAATATTTATATT

CCTAGCTTCTTGAATTAAATTGTTTACATATTCAACGATGTAAAAAATTATTTCTCTATCTA

TTTTCCTTATATCATGCATGGTTTCACATATATCAAAGGATAAAAGCAATCTATGTAAATTA

TCTCACTTTATTAAGTTTTCTATCTGAATTATTGAGAACGTAGATTTCTTTTTGCACTATCC

CCCAATAATTAGCAAAACACACCTAGACTAGATTTGTTTTGCTAACCCAATTGATATTAATT

ATATATGATTAATATTTATATGTATATGGAATTGGTTAATAAAATGCATCTGGTTCATCAAA

GAATTATAAAGACACGTGACATTCATTTAGGATAAGAAATATGGATGATCTCTTTCTCTTAT

TCAGATAATTAGTAATTACACATAACACACAACTTTGATGCCCACATTATAGTGATTAGCAT

GTCACTATGTGTGCATCCTTTTATTTCATACATTAATTAACTTGGCCAATCCAGAAGATGGA

CAAGTCTAGGGTCACATTGCAGGGTACTCTAGCTTACTCGCCTTCTTTTTCGAAGGTTTGAG

TACCTTCAGGGCATCCTCTTGATACATTACTTTCCACTTCGATTGGGGCAAGCTGTAGCAGT

TCTTGCTTAGACCGAATTGCCATCTCACAGAGATGCTGAAGAGTTCGCGACCCTCCAGAAAC

GGTGATACTAACTCCTCGAAACCGAATACTATAGGTACATCCGATCTGGTCGAAACCGAAAA

ATCGAGATGCTGCATAGTTAACCGAATCTCCCGTCCAAGATCCAAGGACTCTGTGCAGTGAA

GCTTCCGTCCTGTCGTATCTGAGATATCTCTTAAATACAACTTTCCCGAAACCCCAGCTTTC

CTTGAAACCAAGGGGATTATCTTGATTCGAATTCGTCTCATCGTTATGTAGCCGCCACTCAG

TCCAACTCGGACTTTCGTCAGGAAGTTTGAAGGGAGAAGTTGTACCTCCTGATCCTCCATCC

CAACGTTCACTGTTAGCTTGTTCCCTAGCGTCGTTTCCTTGTATAGCTCGTTCCATGGATTG

TAAATAGTAATTGTAATGTTGTTTGTTGTTTGTTGTTGTTGGTAATTGTTGTAAAAATACGC

TCTCCAAATGAAATGAACTTCCTTATATAGAGGAAGGGTCTTGCGAAGGATAGTGGGATTGT

GCGTCATCCCTTACGTCAGTGGAGATATCACATCAATCCACTTGCTTTGAAGACGTGGTTGG

AACGTCTTCTTTTTCCACGATGCTCCTCGTGGGTGGGGTCCATCTTTGGGACCACTGTCGG

CAGAGGCATCTTCAACGATGGCCTTTCCTTTATCGCAATGATGGCATTTGTAGGAGCCACCT

TCCTTTTCCACTATCTTCACAATAAAGTGACAGATAGCTGGGCAATGGAATCCGAGGAGTT

TCCGGATATTACCCTTTGTTGAAAAGTCTCAATTGCCCTTTGGTCTTCTGAGACTGTATCTT

TGATATTTTTGGAGTAGACAAGTGTGTCGTGCTCCACCATGTTCTGGCAATTCCGGTTCGCT

TGCTGTCCATAAAACCGCCCAGTCTAGCTATCGCCATGTAAGCCCACTGCAAGCTACCTGCT

TTCTCTTTGCGCTTGCGTTTTCCCTTGTCCAGATAGCCCAGTAGCTGACATTCATCCGGGGT

CAGCACCGTTTCTGCGGACTGGCTTTCTACGTGTTCCGCTTCCTTTTAGCAGCCCTTGCGCCC

TGAGTGCTTGCGGCAGCGTGAAGCTGGCGCGCCGCTCTAGCAGAAGGCATGTTGTTGTGACT
```

-continued

```
CCGAGGGGTTGCCTCAAACTCTATCTTATAACCGGCGTGGAGGCATGGAGGCAAGGGCATTT
TGGTAATTTAAGTAGTTAGTGGAAAATGACGTCATTTACTTAAAGACGAAGTCTTGCGACAA
GGGGGGCCCACGCCGAATTTTAATATTACCGGCGTGGCCCCACCTTATCGCGAGTGCTTTAG
CACGAGCGGTCCAGATTTAAAGTAGAAAAGTTCCCGCCCACTAGGGTTAAAGGTGTTCACAC
TATAAAAGCATATACGATGTGATGGTATTTGATAAAGCGTATATTGTATCAGGTATTTCCGT
CGGATACGAATTATTCGTACGACCCTCCTGCAGGTCAACATGGTGGAGCACGACACACTTGT
CTACTCCAAAAATATCAAAGATACAGTCTCAGAAGACCAAAGGGCAATTGAGACTTTTCAAC
AAAGGGTAATATCCGGAAACCTCCTCGGATTCCATTGCCCAGCTATCTGTCACTTTATTGTG
AAGATAGTGGAAAAGGAAGGTGGCTCCTACAAATGCCATCATTGCGATAAAGGAAAGGCCAT
CGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTG
GAGCACGACACACTTGTCTACTCCAAAAATATCAAAGATACAGTCTCAGAAGACCAAAGGGC
AATTGAGACTTTTCAACAAAGGGTAATATCCGGAAACCTCCTCGGATTCCATTGCCCAGCTA
TCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCC
ACCCACGAGGAGCATCGTGGAAAAAGAAGACGTTCCAACCACGTCTTCAAAGCAAGTGGATT
GATGTGATATCTCCACTGACGTAAGGGATGACGCACAATCCCACTATCCTTCGCAAGACCCT
TCCTCTATATAAGGAAGTTCATTTCATTTGGAGAGGACCTCGAGAAACAAACAAAATCAACA
AATATAGAAAATAACGCATTTCCAATTCTTTGAAATTTCTGCAACATCTAGAACAATGGCTA
ACAAGCACCTCTCATTGTCTCTCTTCCTTGTGCTCCTTGGTCTTTCTGCTTCTCTTGCTTCT
GGTCACCATCACCATCATCACGGATCCGACCCATCCGTGGGAAACAACGTTAAGGAGCTTGT
GGCTTACATCTCCACTTCTGGAGAGAAGGACGCTGGAACCGACGATTACATGTACTTCGGTA
TCAAGACCAAGGATGGAAAGACTCAAGAATGGGAGATGGACAATCCAGGTAACGACTTCATG
GCTGGTAGCAAGGATACTTACACTTTCAAGTTGAAAGACGAGAACCTTAAGATCGACGACAT
CCAGAACATGTGGATTAGGAAACGTAAGTACACCGCCTTCCCAGACGCTTACAAGCCTGAGA
ACATCAAGGTTATCGCTAACGGAAAGGTGGTTGTTGACAAGGATATCAACGAGTGGATTTCT
GGAAACTCCACTTACAACATCAAAGGAGGTTCTGGTGGATCAGGAGGTCCATCTGGAGGTTC
TGGAGGATCCGAGCTTAACGACATCAACAAGATTGAGCTTAAGAACCTCTCCGGAGAGATCA
TCAAGGAGAACGGTAAGGAGGCTATCAAGTACACTTCTTCCGACACCGCTTCCCACAAGGGA
TGGAAGGCCACTCTTTCTGGAACCTTCATCGAAGACCCTCATTCTGACAAGAAGACTGCTTT
GCTTAACCTTGAAGGATTCATCCCATCTGACAAACAGATCTTCGGATCTAAGTACTACGAA
AGATGAAGTGGCCTGAGACTTACAGGATCAACGTGAAGAGCGCTGACGTTAACAACAACATC
AAGATCGCCAACTCTATTCCGAAGAACACTATCGACAAGAAGGACGTGTCCAATTCTATCGG
TTACTCCATCGGAGGTAACATCTCTGTTGAGGGTAAGACTGCTGGTGCTGGAATCAACGCTT
CTTACAACGTTCAGAACACTATCTCCTATGAGCAACCTGACTTCAGAACCATTCAGAGGAAG
GACGATGCTAACCTTGCATCCTGGGACATCAAATTCGTTGAGACTAAGGACGGATACAACAT
CGACTCCTACCATGCTATCTATGGCAACCAGCTCTTCATGAAGAGCAGATTGTACAACAATG
GTGACAAGAACTTCACCGACGATAGGGACCTCTCCACCTTGATCTCTGGTGGATTCTCTCCA
AACATGGCTCTTGCCTTGACCGCTCCTAAGAACGCTAAGGAGTCAGTGATCATCGTTGAATA
CCAGAGGTTCGACAACGACTATATCCTTAACTGGGAGACTACTCAAGCTAGAGGAACTAACA
```

-continued

AGCTTTCTTCAACCTCCGAGTACAACGAGTTTATGTTCAAGATCAACTGGCAGGACCACAAG

ATCGAATACTATCTTTAAGAGCTCGAAGTGACATCACAAAGTTGAAGGTAATAAAGCCAAAT

TAATTAAGACATTTTCATAATGATGTCAAGAATGCAAAGCAAATTGCATAACTGCCTTTATG

CAAAACATTAATATAATATAAATTATAAAGAACTGCGCTCTCTGCTTCTTATTTTCTTAGCT

TCATTTATTAGTCACTAGCTGTTCAGAATTTTCAGTATCTTTTGATATTACTAAGAACCTAA

TCACACAATGTATATTCTTATGCAGGAAAAGCAGAATGCTGAGCTAAAAGAAAGGCTTTTTC

CATTTTCGAGAGACAATGAGAAAGAAGAAGAAGAAGAAGAAGAAGAAGAAGAAAAGAG

TAAATAATAAAGCCCCACAGGAGGCGAAGTTCTTGTAGCTCCATGTTATCTAAGTTATTGAT

ATTGTTTGCCCTATATTTTATTTCTGTCATTGTGTATGTTTTGTTCAGTTTCGATCTCCTTG

CAAAATGCAGAGATTATGAGATGAATAAACTAAGTTATATTATTATACGTGTTAATATTCTC

CTCCTCTCTCTAGCTAGCCTTTTGTTTTCTCTTTTTCTTATTTGATTTTCTTTAAATCAATC

CATTTTAGGAGAGGGCCAGGGAGTGATCCAGCAAAACATGAAGATTAGAAGAAACTTCCCTC

TTTTTTTTCCTGAAAACAATTTAACGTCGAGATTTATCTCTTTTTGTAATGGAATCATTTCT

ACAGTTATGACGAATTCTCGATTAAAAATCCCAATTATATTTGGTCTAATTTAGTTTGGTAT

TGAGTAAAACAAATTCGAACCAAACCAAAATATAAATATATAGTTTTTATATATATGCCTTT

AAGACTTTTATAGAATTTTCTTTAAAAAATATCTAGAAATATTTGCGACTCTTCTGGCATG

TAATATTTCGTTAAATATGAAGTGCTCCATTTTTATTAACTTTAAATAATTGGTTGTACGAT

CACTTTCTTATCAAGTGTTACTAAAATGCGTCAATCTCTTTGTTCTTCCATATTCATATGTC

AAAATCTATCAAATTCTTATATATCTTTTTCGAATTTGAAGTGAAATTTCGATAATTTAAA

ATTAAATAGAACATATCATTATTTAGGTATCATATTGATTTTTATACTTAATTACTAAATTT

GGTTAACTTTGAAAGTGTACATCAACGAAAAATTAGTCAAACGACTAAAATAAATAAATATC

ATGTGTTATTAAGAAAATTCTCCTATAAGAATATTTTAATAGATCATATGTTTGTAAAAAAA

ATTAATTTTTACTAACACATATATTTACTTATCAAAAATTTGACAAAGTAAGATTAAAATAA

TATTCATCTAACAAAAAAAAAACCAGAAAATGCTGAAAACCCGGCAAAACCGAACCAATCCA

AACCGATATAGTTGGTTTGGTTTGATTTTGATATAAACCGAACCAACTCGGTCCATTTGCAC

CCCTAATCATAATAGCTTTAATATTTCAAGATATTATTAAGTTAACGTTGTCAATATCCTGG

AAATTTTGCAAAATGAATCAAGCCTATATGGCTGTAATATGAATTTAAAAGCAGCTCGATGT

GGTGGTAATATGTAATTTACTTGATTCTAAAAAAATATCCCAAGTATTAATAATTTCTGCTA

GGAAGAAGGTTAGCTACGATTTACAGCAAAGCCAGAATACAAAGAACCATAAAGTGATTGAA

GCTCGAAATATACGAAGGAACAAATATTTTTAAAAAAATACGCAATGACTTGGAACAAAGA

AAGTGATATATTTTTTGTTCTTAAACAAGCATCCCCTCTAAAGAATGGCAGTTTTCCTTTGC

ATGTAACTATTATGCTCCCTTCGTTACAAAAATTTTGGACTACTATTGGGAACTTCTTCTGA

AAATAGTGGTACCGAGTGTACTTCAAGTCAGTTGGAAATCAATAAAATGATTATTTTATGAA

TATATTTCATTGTGCAAGTAGATAGAAATTACATATGTTACATAACACACGAATAAACAAA

AAAACACAATCCAAAACAAACACCCCAAACAAAATAACACTATATATATCCTCGTATGAGGA

GAGGCACGTTCAGTGACTCGACGATTCCCGAGCAAAAAAGTCTCCCCGTCACACATATAGT

GGGTGACGCAATTATCTTCAAAGTAATCCTTCTGTTGACTTGTCATTGATAACATCCAGTCT

TCGTCAGGATTGCAAAGAATTATAGAAGGGATCCCACCTTTTATTTTCTTCTTTTTTCCATA

TTTAGGGTTGACAGTGAAATCAGACTGGCAACCTATTAATTGCTTCCACAATGGGACGAACT

TGAAGGGGATGTCGTCGATGATATTATAGGTGGCGTGTTCATCGTAGTTGGTGAAGTCGATG

GTCCCGTTCCAGTAGTTGTGTCGCCCGAGACTTCTAGCCCAGGTGGTCTTTCCGGTACGAGT

-continued

```
TGGTCCGCAGATGTAGAGGCTGGGGTGTCTGACCCCAGTCCTTCCCTCATCCTGGTTAGATC

GGCCATCCACTCAAGGTCAGATTGTGCTTGATCGTAGGAGACAGGATGTATGAAAGTGTAGG

CATCGATGCTTACATGATATAGGTGCGTCTCTCTCCAGTTGTGCAGATCTTCGTGGCAGCGG

AGATCTGATTCTGTGAAGGGCGACACGTACTGCTCAGGTTGTGGAGGAAATAATTTGTTGGC

TGAATATTCCAGCCATTGAAGCTTTGTTGCCCATTCATGAGGGAACTCTTCTTTGATCATGT

CAAGATACTCCTCCTTAGACGTTGCAGTCTGGATAATAGTTCGCCATCGTGCGTCAGATTTG

CGAGGAGACACCTTATGATCTCGGAAATCTCCTCTGGTTTTAATATCTCCGTCCTTTGATAT

GTAATCAAGGACTTGTTTAGAGTTTCTAGCTGGCTGGATATTAGGGTGATTTCCTTCAAAAT

CGAAAAAGAAGGATCCCTAATACAAGGTTTTTTATCAAGCTGGATAAGAGCATGATAGTGG

GTAGTGCCATCTTGATGAAGCTCAGAAGCAACACCAAGGAAGAAAATAAGAAAAGGTGTGAG

TTTCTCCCAGAGAAACTGGAATAAATCATCTCTTTGAGATGAGCACTTGGGGTAGGTAAGGA

AAACATATTTAGATTGGAGTCTGAAGTTCTTGCTAGCAGAAGGCATGTTGTTGTGACTCCGA

GGGGTTGCCTCAAACTCTATCTTATAACCGGCGTGGAGGCATGGAGGCAAGGGCATTTTGGT

AATTTAAGTAGTTAGTGGAAAATGACGTCATTTACTTAAAGACGAAGTCTTGCGACAAGGGG

GGCCCACGCCGAATTTTAATATTACCGGCGTGGCCCCACCTTATCGCGAGTGCTTTAGCACG

AGCGGTCCAGATTTAAAGTAGAAAAGTTCCCGCCCACTAGGGTTAAAGGTGTTCACACTATA

AAAGCATATACGATGTGATGGTATTTGATGGAGCGTATATTGTATCAGGTATTTCCGTCGGA

TACGAATTATTCGTACGGCCGGACCGGTCCCCTAGGCCGGCCAATTCGAGATCGGCCGCGGC

TGAGTGGCTCCTTCAATCGTTGCGGTTCTGTCAGTTCCAAACGTAAAACGGCTTGTCCCGCG

TCATCGGCGGGGGTCATAACGTGACTCCCTTAATTCTCCGCTCATGATCAGATTGTCGTTTC

CCGCCTTCAGTTTAAACTATCAGTGTTTGACAGGATATATTGGCGGGTAAACCTAAGAGAAA

AGAGCGTTTATTAGAATAATCGGATATTTAAAAGGGCGTGAAAAGGTTTATCCGTTCGTCCA

TTTGTATGTGCATGCCAACCACAGGGTTCCCCAGATCTGGCGCCGGCCAGCGAGACGAGCAA

GATTGGCCGCCGCCCGAAACGATCCGACAGCGCGCCCAGCACAGGTGCGCAGGCAAATTGCA

CCAACGCATACAGCGCCAGCAGAATGCCATAGTGGGCGGTGACGTCGTTCGAGTGAACCAGA

TCGCGCAGGAGGCCCGGCAGCACCGGCATAATCAGGCCGATGCCGACAGCGTCGAGCGCGAC

AGTGCTCAGAATTACGATCAGGGGTATGTTGGGTTTCACGTCTGGCCTCCGGAGACTGTCAT

ACGCGTAAAAAGGCCGCGTTGCTGGCGTTTTTCCATAGGCTCCGCCCCCCTGACGAGCATCA

CAAAAATCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCTACAGAGTT

CTTGAAGTGGTGGCCTAACTACGGCTACACTAGAAGGACAGTATTTGGTATCTGCGCTCTGC

TGAAGCCAGTTACCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTAAGGGA

TTTTGGTCATGAGATTATCAAAAAGGATCTTCACCTAGATCCTTTTAAATTAAAAATGAAGT

TTTAAATCAATCTAAAGTATATATGAGTAAACTTGGTCTGCAGTTGCCATGTTTTACGGCAG
```

-continued

```
TGAGAGCAGAGATAGCGCTGATGTCCGGCGGTGCTTTTGCCGTTACGCACCACCCCGTCAGT
AGCTGAACAGGAGGGACAGCTGATAGACACAGAAGCCACTGGAGCACCTCAAAAACACCATC
ATACACTAAATCAGTAAGTTGGCAGCATCACCCATAATTGTGGTTTCAAAATCGGCTCCGTC
GATACTATGTTATACGCCAACTTTGAAAACAACTTTGAAAAAGCTGTTTTCTGGTATTTAAG
GTTTTAGAATGCAAGGAACAGTGAATTGGAGTTCGTCTTGTTATAATTAGCTTCTTGGGGTA
TCTTTAAATACTGTAGAAAAGAGGAAGGAAATAATAAATGGCTAAAATGAGAATATCACCGG
AATTGAAAAAACTGATCGAAAAATACCGCTGCGTAAAAGATACGGAAGGAATGTCTCCTGCT
AAGGTATATAAGCTGGTGGGAGAAAATGAAAACCTATATTTAAAAATGACGGACAGCCGGTA
TAAAGGGACCACCTATGATGTGGAACGGGAAAAGGACATGATGCTATGGCTGGAAGGAAAGC
TGCCTGTTCCAAAGGTCCTGCACTTTGAACGGCATGATGGCTGGAGCAATCTGCTCATGAGT
GAGGCCGATGGCGTCCTTTGCTCGGAAGAGTATGAAGATGAACAAAGCCCTGAAAAGATTAT
CGAGCTGTATGCGGAGTGCATCAGGCTCTTTCACTCCATCGACATATCGGATTGTCCCTATA
CGAATAGCTTAGACAGCCGCTTAGCCGAATTGGATTACTTACTGAATAACGATCTGGCCGAT
GTGGATTGCGAAAACTGGGAAGAAGACACTCCATTTAAAGATCCGCGCGAGCTGTATGATTT
TTTAAAGACGGAAAAGCCCGAAGAGGAACTTGTCTTTTCCCACGGCGACCTGGGAGACAGCA
ACATCTTTGTGAAAGATGGCAAAGTAAGTGGCTTTATTGATCTTGGGAGAAGCGGCAGGGCG
GACAAGTGGTATGACATTGCCTTCTGCGTCCGGTCGATCAGGGAGGATATCGGGAAGAACA
GTATGTCGAGCTATTTTTTGACTTACTGGGGATCAAGCCTGATTGGGAGAAAATAAAATATT
ATATTTTACTGGATGAATTGTTTTAGTACCTAGATGTGGCGCAACGATGCCGGCGACAAGCA
GGAGCGCACCGACTTCTTCCGCATCAAGTGTTTTGGCTCTCAGGCCGAGGCCCACGGCAAGT
ATTTGGGCAAGGGGTCGCTGGTATTCGTGCAGGGCAAGATTCGGAATACCAAGTACGAGAAG
GACGGCCAGACGGTCTACGGGACCGACTTCATTGCCGATAAGGTGGATTATCTGGACACCAA
GGCACCAGGCGGGTCAAATCAGGAATAAGGGCACATTGCCCCGGCGTGAGTCGGGGCAATCC
CGCAAGGAGGGTGAATGAATCGGACGTTTGACCGGAAGGCATACAGGCAAGAACTGATCGAC
GCGGGGTTTTCCGCCGAGGATGCCGAAACCATCGCAAGCCGCACCGTCATGCGTGCGCCCCG
CGAAACCTTCCAGTCCGTCGGCTCGATGGTCCAGCAAGCTACGGCCAAGATCGAGCGCGACA
GCGTGCAACTGGCTCCCCCTGCCCTGCCCGCGCCATCGGCCGCCGTGGAGCGTTCGCGTCGT
CTCGAACAGGAGGCGGCAGGTTTGGCGAAGTCGATGACCATCGACACGCGAGGAACTATGAC
GACCAAGAAGCGAAAAACCGCCGGCGAGGACCTGGCAAAACAGGTCAGCGAGGCCAAGCAGG
CCGCGTTGCTGAAACACACGAAGCAGCAGATCAAGGAAATGCAGCTTTCCTTGTTCGATATT
GCGCCGTGGCCGGACACGATGCGAGCGATGCCAAACGACACGGCCCGCTCTGCCCTGTTCAC
CACGCGCAACAAGAAAATCCCGCGCGAGGCGCTGCAAAACAAGGTCATTTTCCACGTCAACA
AGGACGTGAAGATCACCTACACCGGCGTCGAGCTGCGGGCCGACGATGACGAACTGGTGTGG
CAGCAGGTGTTGGAGTACGCGAAGCGCACCCCTATCGGCGAGCCGATCACCTTCACGTTCTA
CGAGCTTTGCCAGGACCTGGGCTGGTCGATCAATGGCCGGTATTACACGAAGGCCGAGGAAT
GCCTGTCGCGCCTACAGGCGACGGCGATGGGCTTCACGTCCGACCGCGTTGGGCACCTGGAA
TCGGTGTCGCTGCTGCACCGCTTCCGCGTCCTGGACCGTGGCAAGAAAACGTCCCGTTGCCA
GGTCCTGATCGACGAGGAAATCGTCGTGCTGTTTGCTGGCGACCACTACACGAAATTCATAT
GGGAGAAGTACCGCAAGCTGTCGCCGACGGCCCGACGGATGTTCGACTATTTCAGCTCGCAC
CGGGAGCCGTACCCGCTCAAGCTGGAAACCTTCCGCCTCATGTGCGGATCGGATTCCACCCG
CGTGAAGAAGTGGCGCGAGCAGGTCGGCGAAGCCTGCGAAGAGTTGCGAGGCAGCGGCCTGG
```

```
TGGAACACGCCTGGGTCAATGATGACCTGGTGCATTGCAAACGCTAGGGCCTTGTGGGGTCA

GTTCCGGCTGGGGGTTCAGCAGCCAGCGCTTTACTGGCATTTCAGGAACAAGCGGGCACTGC

TCGACGCACTTGCTTCGCTCAGTATCGCTCGGGACGCACGGCGCGCTCTACGAACTGCCGAT

AAACAGAGGATTAAAATTGACAATTCAATGGCAAGGACTGCCAGCGCTGCCATTTTTGGGGT

GAGGCCGTTCGCGGCCGAGGGGCGCAGCCCCTGGGGGATGGGAGGCCCGCGTTAGCGGGCC

GGGAGGGTTCGAGAAGGGGGGGCACCCCCCTTCGGCGTGCGCGGTCACGCGCACAGGGCGCA

GCCCTGGTTAAAAACAAGGTTTATAAATATTGGTTTAAAAGCAGGTTAAAAGACAGGTTAGC

GGTGGCCGAAAAACGGGCGGAAACCCTTGCAAATGCTGGATTTTCTGCCTGTGGACAGCCCC

TCAAATGTCAATAGGTGCGCCCCTCATCTGTCAGCACTCTGCCCCTCAAGTGTCAAGGATCG

CGCCCCTCATCTGTCAGTAGTCGCGCCCCTCAAGTGTCAATACCGCAGGGCACTTATCCCCA

GGCTTGTCCACATCATCTGTGGGAAACTCGCGTAAAATCAGGCGTTTTCGCCGATTTGCGAG

GCTGGCCAGCTCCACGTCGCCGGCCGAAATCGAGCCTGCCCCTCATCTGTCAACGCCGCGCC

GGGTGAGTCGGCCCCTCAAGTGTCAACGTCCGCCCCTCATCTGTCAGTGAGGGCCAAGTTTT

CCGCGAGGTATCCACAACGCCGGCGGCCGCGGTGTCTCGCACACGGCTTCGACGGCGTTTCT

GGCGCGTTTGCAGGGCCATAGACGGCCGCCAGCCCAGCGGCGAGGGCAACCAGCCCGGTGAG

CGTCGCAAAGGCGCTCGGTCTTGCCTTGCTCGTCGAGATCTGGGGTCGATCAGCCGGGGATG

CATCAGGCCGACAGTCGGAACTTCGGGTCCCCGACCTGTACCATTCGGTGAGCAATGGATAG

GGGAGTTGATATCGTCAACGTTCACTTCTAAAGAAATAGCGCCACTCAGCTTCCTCAGCGGC

TTTATCCAGCGATTTCCTATTATGTCGGCATAGTTCTCAAGATCGACAGCCTGTCACGGTTA

AGCGAGAAATGAATAAGAAGGCTGATAATTCGGATCTCTGCGAGGGAGATGATATTTGATCA

CAGGCAGCAACGCTCTGTCATCGTTACAATCAACATGCTACCCTCCGCGAGATCATCCGTGT

TTCAAACCCGGCAGCTTAGTTGCCGTTCTTCCGAATAGCATCGGTAACATGAGCAAAGTCTG

CCGCCTTACAACGGCTCTCCCGCTGACGCCGTCCCGGACTGATGGGCTGCCTGTATCGAGTG

GTGATTTTGTGCCGAGCTGCCGGTCGGGGAGCTGTTGGCTGGCTGGTGGCAGGATATATTGT

GGTGTAAACAAATTGACGCTTAGACAACTTAATAACACATTGCGGACGTTTTTAATGTACTG

GGGTGGTTTTTCTTTTCACCAGTGAGACGGGCAACAGCTGATTGCCCTTCACCGCCTGGCCC

TGAGAGAGTTGCAGCAAGCGGTCCACGCTGGTTTGCCCCAGCAGGCGAAAATCCTGTTTGAT

GGTGGTTCCGAAATCGGCAAAATCCCTTATAAATCAAAAGAATAGCCCGAGATAGGGTTGAG

TGTTGTTCCAGTTTGGAACAAGAGTCCACTATTAAAGAACGTGGACTCCAACGTCAAAGGGC

GAAAAACCGTCTATCAGGGCGATGGCCCACTACGTGAACCATCACCCAAATCAAGTTTTTTG

GGGTCGAGGTGCCGTAAAGCACTAAATCGGAACCCTAAAGGGAGCCCCCGATTTAGAGCTTG

ACGGGGAAAGCCGGCGAACGTGGCGAGAAAGGAAGGGAAGAAAGCGAAAGGAGCGGGCGCCA

TTCAGGCTGCGCAACTGTTGGGAAGGG
```

The sequence indicated in bold above is the portion that encodes the fusion protein:
(SEQ ID NO: 6)

```
ATGGCTAACAAGCACCTCTCATTGTCTCTCTTCCTTGTGCTCCTTGGTCTTTCTGCT

TCTCTTGCTTCTGGTCACCATCACCATCATCACGGATCCGACCCATCCGTGGGAAACAACGT

TAAGGAGCTTGTGGCTTACATCTCCACTTCTGGAGAGAAGGACGCTGGAACCGACGATTACA

TGTACTTCGGTATCAAGACCAAGGATGGAAAGACTCAAGAATGGGAGATGGACAATCCAGGT

AACGACTTCATGGCTGGTAGCAAGGATACTTACACTTTCAAGTTGAAAGACGAGAACCTTAA

GATCGACGACATCCAGAACATGTGGATTAGGAAACGTAAGTACACCGCCTTCCCAGACGCTT
```

```
-continued
ACAAGCCTGAGAACATCAAGGTTATCGCTAACGGAAAGGTGGTTGTTGACAAGGATATCAAC

GAGTGGATTTCTGGAAACTCCACTTACAACATCAAAGGAGGTTCTGGTGGATCAGGAGGTCC

ATCTGGAGGTTCTGGAGGATCCGAGCTTAACGACATCAACAAGATTGAGCTTAAGAACCTCT

CCGGAGAGATCATCAAGGAGAACGGTAAGGAGGCTATCAAGTACACTTCTTCCGACACCGCT

TCCCACAAGGGATGGAAGGCCACTCTTTCTGGAACCTTCATCGAAGACCCTCATTCTGACAA

GAAGACTGCTTTGCTTAACCTTGAAGGATTCATCCCATCTGACAAACAGATCTTCGGATCTA

AGTACTACGGAAAGATGAAGTGGCCTGAGACTTACAGGATCAACGTGAAGAGCGCTGACGTT

AACAACAACATCAAGATCGCCAACTCTATTCCGAAGAACACTATCGACAAGAAGGACGTGTC

CAATTCTATCGGTTACTCCATCGGAGGTAACATCTCTGTTGAGGGTAAGACTGCTGGTGCTG

GAATCAACGCTTCTTACAACGTTCAGAACACTATCTCCTATGAGCAACCTGACTTCAGAACC

ATTCAGAGGAAGGACGATGCTAACCTTGCATCCTGGGACATCAAATTCGTTGAGACTAAGGA

CGGATACAACATCGACTCCTACCATGCTATCTATGGCAACCAGCTCTTCATGAAGAGCAGAT

TGTACAACAATGGTGACAAGAACTTCACCGACGATAGGGACCTCTCCACCTTGATCTCTGGT

GGATTCTCTCCAAACATGGCTCTTGCCTTGACCGCTCCTAAGAACGCTAAGGAGTCAGTGAT

CATCGTTGAATACCAGAGGTTCGACAACGACTATATCCTTAACTGGGAGACTACTCAAGCTA

GAGGAACTAACAAGCTTTCTTCAACCTCCGAGTACAACGAGTTTATGTTCAAGATCAACTGG

CAGGACCACAAGATCGAATACTATCTTTAA
```

The proteins of the present invention may be expressed from an isolated DNA sequence encoding the protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell or bacteriophage. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

Expression Cassettes

In certain embodiments, the present invention provides an expression cassette comprising the nucleic acid described herein and a promoter.

In certain embodiments, the promoter is a plant promoter.

In certain embodiments, the plant promoter is operable in corn or rice.

In certain embodiments, the plant promoter is operable in seed tissue.

In certain embodiments, the seed tissue is embryo or endosperm tissue.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a known mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world-wide-web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78% or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about 5EC lower than the $T_m$ for the specific sequence at a defined ionic strength and pH.

An example of highly stringent wash conditions is 0.15 M NaCl at 72EC for about 15 minutes. An example of stringent wash conditions is a 0.2×SSC wash at 65EC for 15 minutes. Often, a high stringency wash is preceded by a low stringency wash to remove background probe signal. An example medium stringency wash for a duplex of, e.g., more than 100 nucleotides, is 1×SSC at 45EC for 15 minutes. An example low stringency wash for a duplex of, e.g., more than 100 nucleotides, is 4-6×SSC at 40EC for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30EC and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

In certain embodiments, the nucleic acid sequences are the following:

```
Fusion protein cds, with signal peptide:
                                           (SEQ ID NO: 7)
ATGGCTAACAAGCACCTCTCATTGTCTCTCTTCCTTGTGCTCCTTGGTCTTTCTGCTTCTCT

TGCTTCTGGTCACCATCACCATCATCACGGATCCGACCCATCCGTGGGAAACAACGTTAAGG

AGCTTGTGGCTTACATCTCCACTTCTGGAGAGAAGGACGCTGGAACCGACGATTACATGTAC

TTCGGTATCAAGACCAAGGATGGAAAGACTCAAGAATGGGAGATGGACAATCCAGGTAACGA

CTTCATGGCTGGTAGCAAGGATACTTACACTTTCAAGTTGAAAGACGAGAACCTTAAGATCG

ACGACATCCAGAACATGTGGATTAGGAAACGTAAGTACACCGCCTTCCCAGACGCTTACAAG

CCTGAGAACATCAAGGTTATCGCTAACGGAAAGGTGGTTGTTGACAAGGATATCAACGAGTG

GATTTCTGGAAACTCCACTTACAACATCAAAGGAGGTTCTGGTGGATCAGGAGGTCCATCTG

GAGGTTCTGGAGGATCCGAGCTTAACGACATCAACAAGATTGAGCTTAAGAACCTCTCCGGA

GAGATCATCAAGGAGAACGGTAAGGAGGCTATCAAGTACACTTCTTCCGACACCGCTTCCCA

CAAGGGATGGAAGGCCACTCTTTCTGGAACCTTCATCGAAGACCCTCATTCTGACAAGAAGA

CTGCTTTGCTTAACCTTGAAGGATTCATCCCATCTGACAAACAGATCTTCGGATCTAAGTAC
```

-continued

```
TACGGAAAGATGAAGTGGCCTGAGACTTACAGGATCAACGTGAAGAGCGCTGACGTTAACAA

CAACATCAAGATCGCCAACTCTATTCCGAAGAACACTATCGACAAGAAGGACGTGTCCAATT

CTATCGGTTACTCCATCGGAGGTAACATCTCTGTTGAGGGTAAGACTGCTGGTGCTGGAATC

AACGCTTCTTACAACGTTCAGAACACTATCTCCTATGAGCAACCTGACTTCAGAACCATTCA

GAGGAAGGACGATGCTAACCTTGCATCCTGGGACATCAAATTCGTTGAGACTAAGGACGGAT

ACAACATCGACTCCTACCATGCTATCTATGGCAACCAGCTCTTCATGAAGAGCAGATTGTAC

AACAATGGTGACAAGAACTTCACCGACGATAGGGACCTCTCCACCTTGATCTCTGGTGGATT

CTCTCCAAACATGGCTCTTGCCTTGACCGCTCCTAAGAACGCTAAGGAGTCAGTGATCATCG

TTGAATACCAGAGGTTCGACAACGACTATATCCTTAACTGGGAGACTACTCAAGCTAGAGGA

ACTAACAAGCTTTCTTCAACCTCCGAGTACAACGAGTTTATGTTCAAGATCAACTGGCAGGA

CCACAAGATCGAATACTATCTT
```

Fusion protein cds, without signal peptide:
(SEQ ID NO: 8)
```
ATGGCTCACCATCACCATCATCACGGATCCGACCCATCCGTGGGAAACAACGTTAAGGAGCT

TGTGGCTTACATCTCCACTTCTGGAGAGAAGGACGCTGGAACCGACGATTACATGTACTTCG

GTATCAAGACCAAGGATGGAAAGACTCAAGAATGGGAGATGGACAATCCAGGTAACGACTTC

ATGGCTGGTAGCAAGGATACTTACACTTTCAAGTTGAAAGACGAGAACCTTAAGATCGACGA

CATCCAGAACATGTGGATTAGGAAACGTAAGTACACCGCCTTCCCAGACGCTTACAAGCCTG

AGAACATCAAGGTTATCGCTAACGGAAAGGTGGTTGTTGACAAGGATATCAACGAGTGGATT

TCTGGAAACTCCACTTACAACATCAAAGGAGGTTCTGGTGGATCAGGAGGTCCATCTGGAGG

TTCTGGAGGATCCGAGCTTAACGACATCAACAAGATTGAGCTTAAGAACCTCTCCGGAGAGA

TCATCAAGGAGAACGGTAAGGAGGCTATCAAGTACACTTCTTCCGACACCGCTTCCCACAAG

GGATGGAAGGCCACTCTTTCTGGAACCTTCATCGAAGACCCTCATTCTGACAAGAAGACTGC

TTTGCTTAACCTTGAAGGATTCATCCCATCTGACAAACAGATCTTCGGATCTAAGTACTACG

GAAAGATGAAGTGGCCTGAGACTTACAGGATCAACGTGAAGAGCGCTGACGTTAACAACAAC

ATCAAGATCGCCAACTCTATTCCGAAGAACACTATCGACAAGAAGGACGTGTCCAATTCTAT

CGGTTACTCCATCGGAGGTAACATCTCTGTTGAGGGTAAGACTGCTGGTGCTGGAATCAACG

CTTCTTACAACGTTCAGAACACTATCTCCTATGAGCAACCTGACTTCAGAACCATTCAGAGG

AAGGACGATGCTAACCTTGCATCCTGGGACATCAAATTCGTTGAGACTAAGGACGGATACAA

CATCGACTCCTACCATGCTATCTATGGCAACCAGCTCTTCATGAAGAGCAGATTGTACAACA

ATGGTGACAAGAACTTCACCGACGATAGGGACCTCTCCACCTTGATCTCTGGTGGATTCTCT

CCAAACATGGCTCTTGCCTTGACCGCTCCTAAGAACGCTAAGGAGTCAGTGATCATCGTTGA

ATACCAGAGGTTCGACAACGACTATATCCTTAACTGGGAGACTACTCAAGCTAGAGGAACTA

ACAAGCTTTCTTCAACCTCCGAGTACAACGAGTTTATGTTCAAGATCAACTGGCAGGACCAC

AAGATCGAATACTATCTT
```

6His-plcC, with signal peptide:
(SEQ ID NO: 9)
```
ATGGCTAACAAGCACCTCTCATTGTCTCTCTTCCTTGTGCTCCTTGGTCTTTCTGCTTCTCT

TGCTTCTGGTCACCATCACCATCATCACGGATCCGACCCATCCGTGGGAAACAACGTTAAGG

AGCTTGTGGCTTACATCTCCACTTCTGGAGAGAAGGACGCTGGAACCGACGATTACATGTAC

TTCGGTATCAAGACCAAGGATGGAAAGACTCAAGAATGGGAGATGGACAATCCAGGTAACGA

CTTCATGGCTGGTAGCAAGGATACTTACACTTTCAAGTTGAAAGACGAGAACCTTAAGATCG

ACGACATCCAGAACATGTGGATTAGGAAACGTAAGTACACCGCCTTCCCAGACGCTTACAAG
```

-continued

CCTGAGAACATCAAGGTTATCGCTAACGGAAAGGTGGTTGTTGACAAGGATATCAACGAGTG

GATTTCTGGAAACTCCACTTACAACATCAAA

6His-plcC, without signal peptide:
(SEQ ID NO: 10)
ATGGCTCACCATCACCATCATCACGGATCCGACCCATCCGTGGGAAACAACGTTAAGGAGCT

TGTGGCTTACATCTCCACTTCTGGAGAGAAGGACGCTGGAACCGACGATTACATGTACTTCG

GTATCAAGACCAAGGATGGAAAGACTCAAGAATGGGAGATGGACAATCCAGGTAACGACTTC

ATGGCTGGTAGCAAGGATACTTACACTTTCAAGTTGAAAGACGAGAACCTTAAGATCGACGA

CATCCAGAACATGTGGATTAGGAAACGTAAGTACACCGCCTTCCCAGACGCTTACAAGCCTG

AGAACATCAAGGTTATCGCTAACGGAAAGGTGGTTGTTGACAAGGATATCAACGAGTGGATT

TCTGGAAACTCCACTTACAACATCAAA

6His-netB, with signal peptide:
(SEQ ID NO: 11)
ATGGCTAACAAGCACCTCTCATTGTCTCTCTTCCTTGTGCTCCTTGGTCTTTCTGCTTCTCT

TGCTTCTGGTCACCATCACCATCATCACGGATCCGAGCTTAACGACATCAACAAGATTGAGC

TTAAGAACCTCTCCGGAGAGATCATCAAGGAGAACGGTAAGGAGGCTATCAAGTACACTTCT

TCCGACACCGCTTCCCACAAGGGATGGAAGGCCACTCTTTCTGGAACCTTCATCGAAGACCC

TCATTCTGACAAGAAGACTGCTTTGCTTAACCTTGAAGGATTCATCCCATCTGACAAACAGA

TCTTCGGATCTAAGTACTACGGAAAGATGAAGTGGCCTGAGACTTACAGGATCAACGTGAAG

AGCGCTGACGTTAACAACAACATCAAGATCGCCAACTCTATTCCGAAGAACACTATCGACAA

GAAGGACGTGTCCAATTCTATCGGTTACTCCATCGGAGGTAACATCTCTGTTGAGGGTAAGA

CTGCTGGTGCTGGAATCAACGCTTCTTACAACGTTCAGAACACTATCTCCTATGAGCAACCT

GACTTCAGAACCATTCAGAGGAAGGACGATGCTAACCTTGCATCCTGGGACATCAAATTCGT

TGAGACTAAGGACGGATACAACATCGACTCCTACCATGCTATCTATGGCAACCAGCTCTTCA

TGAAGAGCAGATTGTACAACAATGGTGACAAGAACTTCACCGACGATAGGGACCTCTCCACC

TTGATCTCTGGTGGATTCTCTCCAAACATGGCTCTTGCCTTGACCGCTCCTAAGAACGCTAA

GGAGTCAGTGATCATCGTTGAATACCAGAGGTTCGACAACGACTATATCCTTAACTGGGAGA

CTACTCAAGCTAGAGGAACTAACAAGCTTTCTTCAACCTCCGAGTACAACGAGTTTATGTTC

AAGATCAACTGGCAGGACCACAAGATCGAATACTATCTT

6His-netB, without signal peptide:
(SEQ ID NO: 12)
ATGGCTCACCATCACCATCATCACGGATCCGAGCTTAACGACATCAACAAGATTGAGCTTAA

GAACCTCTCCGGAGAGATCATCAAGGAGAACGGTAAGGAGGCTATCAAGTACACTTCTTCCG

ACACCGCTTCCCACAAGGGATGGAAGGCCACTCTTTCTGGAACCTTCATCGAAGACCCTCAT

TCTGACAAGAAGACTGCTTTGCTTAACCTTGAAGGATTCATCCCATCTGACAAACAGATCTT

CGGATCTAAGTACTACGGAAAGATGAAGTGGCCTGAGACTTACAGGATCAACGTGAAGAGCG

CTGACGTTAACAACAACATCAAGATCGCCAACTCTATTCCGAAGAACACTATCGACAAGAAG

GACGTGTCCAATTCTATCGGTTACTCCATCGGAGGTAACATCTCTGTTGAGGGTAAGACTGC

TGGTGCTGGAATCAACGCTTCTTACAACGTTCAGAACACTATCTCCTATGAGCAACCTGACT

TCAGAACCATTCAGAGGAAGGACGATGCTAACCTTGCATCCTGGGACATCAAATTCGTTGAG

ACTAAGGACGGATACAACATCGACTCCTACCATGCTATCTATGGCAACCAGCTCTTCATGAA

GAGCAGATTGTACAACAATGGTGACAAGAACTTCACCGACGATAGGGACCTCTCCACCTTGA

TCTCTGGTGGATTCTCTCCAAACATGGCTCTTGCCTTGACCGCTCCTAAGAACGCTAAGGAG

-continued

```
TCAGTGATCATCGTTGAATACCAGAGGTTCGACAACGACTATATCCTTAACTGGGAGACTAC

TCAAGCTAGAGGAACTAACAAGCTTTCTTCAACCTCCGAGTACAACGAGTTTATGTTCAAGA

TCAACTGGCAGGACCACAAGATCGAATACTATCTT
```

Vectors

In certain embodiments, the present invention provides a recombinant vector comprising the expression cassette described herein and a vector.

In certain embodiments, the vector is a viral vector.

In certain embodiments, the vector is a bean yellow dwarf virus replicon.

In certain embodiments, the vector is pBYR2eK2M-6HplcCnetB. (SEQ ID NO: 14 and FIG. 6).

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

Plant Cells and Animal Feed

In certain embodiments, the present invention provides a plant cell comprising the antigenic protein described herein, the nucleic acid described herein, the expression cassette described herein or the recombinant vector described herein.

In certain embodiments, the plant is a corn or rice cell.

In certain embodiments, the plant cell further comprises an *E. coli* heat-labile enterotoxin (LT) and/or a cholera toxin (CT).

In certain embodiments, the present invention provides animal feed comprising the plant cell described herein.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

Vaccines

In certain embodiments, the present invention provides a vaccine comprising the antigenic protein described herein, the nucleic acid described herein, the expression cassette described herein, the recombinant vector described herein, the plant cell described herein, or the animal feed described herein.

The fusion antigen was readily purified using metal affinity chromatography, and used for chicken immunization experiments. The data indicate that the plant-made fusion protein was immunogenic and protective. Evidence was observed on western blots that the PlcC-NetB accumulated in several glycosylated forms. A search of the PlcC-NetB amino acid sequence for consensus Asn-linked glycosylation sites (Asn-X-Ser/Thr) showed one site in the PlcC and four sites in the NetB domain. Mapping of these sites on the 3-dimensional structures of Plc and NetB showed that they mostly occur in surface loops, and thus probably would not interfere with correct folding of the proteins or impair the antigen structure of protective epitopes. In some cases, such eukaryotic glycosylation was shown to be either neutral in effect or enhance immunogenicity of plant-made antigens. However, it is difficult to predict the effects of glycosylation on the immunogenicity of PlcC-NetB. The preliminary study showed it is immunogenic in chickens, it is possible that a non-glycosylated protein will be even more potent.

Thus, a new expression vector was constructed that lacks the N-terminal signal sequence, which resulted in cytosolic accumulation and thus unglycosylated antigen. The glycosylated and unglycosylated antigens are used in further studies to test immunogenicity and protection in chickens. Several mutant forms of NetB have been studied and showed reduced toxicity and may retain protective immunogenicity. Single amino acid substitutions in the rim loop region that significantly reduce its toxicity include Y191A, R200A, W257A, W262A S254L, R230Q and W287R. Some of these were shown to retain the ability to generate protective immune responses, including W262A and S254L. Thus it is reasonable to contemplate the use of multiple different mutations in the NetB component of the PlcCNetB fusion protein, in order to maximize its safety. For production of the fusion protein in seeds of corn or rice, stable transgenic lines must be developed. The expression construct would use an appropriate promoter that will drive strong expression in a seed tissue, such as embryo or endosperm tissues. *Agrobacterium*-mediated delivery of DNA to embryogenic cell cultures enables creation of stably transformed whole plants that transmit the transgenes to sexual progeny.

One may consider the co-delivery of a mucosal adjuvant to enhance immunogenicity of the PlcC-NetB antigens. The *E. coli* heat-labile enterotoxin (LT) and related cholera toxin (CT) are potent stimulators of mucosal immunity. LT and mutants thereof (including LTA S63K and A72R have been expressed in transgenic tobacco cells, and were well tolerated and immunogenic in chickens by oral or parenteral delivery. Orally immunogenic LT-B was expressed in transgenic corn; and CT-B was expressed in transgenic rice. Methods for milling and formulating corn and rice for oral delivery are well developed and convenient.

Methods of Administration

In certain embodiments, the present invention provides a method of protecting an avian species from *C. perfringens* infections comprising administering the vaccine described herein.

In certain embodiments, the avian species is chicken, turkey, duck or ostrich.

In certain embodiments, the avian is a chicken or turkey.

The present invention also provides a method of protecting poultry by administering to the poultry an immunologically protective amount of a vaccine of the present invention. As used herein, the term "immunologically protective" means that the vaccine is effective in inducing a protective immune response. An immunological response to a composition or vaccine is the development in the host of a cellular and/or antibody-mediated immune response to the protein or vaccine of interest. Usually, such a response consists of the subject producing antibodies, B cell, helper T cells, suppressor T cells, and/or cytotoxic T cells directed specifically to an antigen or antigens included in the composition or vaccine of interest.

The fusion can be purified and used to inject birds. Injections can be given to hens prior to lay, to enhance immunity of chicks during the first 2-3 weeks of life by passive transfer of antibodies against the fusion protein. In certain embodiments, a suitable adjuvant is used. For example, saponin adjuvant such as Quil A, various oil emulsion adjuvants such as water in oil or water in oil in water formulations are used.

The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of therapeutic agents may be accomplished through the administration of the therapeutic agent, such as a fusion protein. Pharmaceutical formulations, dosages and routes of administration for peptide are generally known.

The present invention envisions treating uveitis in a mammal by the administration of an agent, e.g., a fusion protein. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intraocular routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 saline solutions and water.

As used herein, the term "therapeutic agent" refers to a fusion protein agent or material containing the fusion protein that has a beneficial effect on the mammalian recipient. "Treating" as used herein refers to preventing infection of *C. perfringens* infection.

The present invention also provides a method of protecting poultry by administering a vaccine that is effective in inducing cellular and humoral immunity and that contains a biological agent or microbial component that is effective in stimulating a protective cellular and humoral immune response to *C. perfringens*.

The purified protein can also be used for in ovo vaccination. Again, a suitable adjuvant may be used to enhance immunogenicity, as discussed above. The vaccine of the present invention can be administered via conventional modes of administration or in ovo. Methods of in ovo immunization are set forth, for example, in U.S. Pat. No. 6,048,535. Vaccination can be performed at any age. For in ovo vaccination, vaccination would be done in the last quarter of embryonal development but may be done at any time during embryonation. The vaccines according to the invention can, for example, be administered intramuscularly, subcutaneously, orally, intraocularly, intratracheally, intranasally, in ovo, in drinking water, in the form of sprays or by contact spread. Preferably, chickens are given the first vaccine in ovo or at one day of age. Subsequent vaccinations are done according to need. Breeder chickens can be vaccinated before and during the lay cycle (several inoculations).

In certain embodiments, the vaccine is administered in poultry feed.

In certain embodiments, the vaccine is administered by injection.

In certain embodiments, the vaccine is administered in ovo.

Adjuvants

Vaccines are often formulated and inoculated with various adjuvants. The adjuvants aid in attaining a more durable and higher level of immunity using small amounts of antigen or fewer doses than if the immunogen were administered alone. The mechanism of adjuvant action is complex, and may involve the stimulation of cytokine production, phagocytosis and other activities of the reticuloendothelial system as well as a delayed release and degradation of the antigen. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecylglycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of $E.\ coli$ heat labile toxin or of the cholera toxin, and mutant forms of complete toxin in which mutations have been introduced into the A subunit of $E.\ coli$ heat labile toxin or cholera toxin that attenuate its toxicity while retaining its adjuvant properties. McGhee, J. R., et al., "On vaccine development," $Sem.\ Hematol.$, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

In certain embodiments, a saponin adjuvant such as Quil A, various oil emulsion adjuvants such as water in oil or water in oil in water formulations are used.

The invention will now be illustrated by the following non-limiting Example.

Example 1

Introduction $Clostridium\ perfringens$ (C. perfringens) induced necrotic enteritis (NE) is becoming an economically significant problem for the broiler industry. The acute form of the disease leads to increased mortality in broiler flocks, which can account for high losses of up to 1% per day, reaching mortality rates up to 10-40%. In the subclinical form, fibrin deposits and other damage to the intestinal mucosa caused by C. perfringens (FIG. 1) leads to poor productivity (reduced growth, reduced feed efficiency) without mortality. C. perfringens-infected poultry also constitutes a risk for transmission to humans through the food chain. Historically, C. perfringens outbreaks in the broiler industry were avoided by the use of growth-promoting antimicrobials in the diet. However, concerns regarding antibiotic resistance led to restrictions on the use of antibiotics. This, coupled with high-density living conditions and the reuse of litter materials, has culminated in a resurgence of C. perfringens infections, estimated to cause a global economic loss of over $US2 billion annually.

C. perfringens is a Gram-positive anaerobic spore-forming bacterium. At least 17 exotoxins and enzymes responsible for the associated lesions and disease symptoms have been identified. C. perfringens strains are classified into five types (A, B, C, D and E), based on their ability to produce different combinations of four major toxins ($\alpha$, $\beta$, $\epsilon$ and $\iota$). NE and the subclinical form of C. perfringens infection in poultry are caused by C. perfringens type A strains. For many years, the chromosome-encoded alpha-toxin, a membrane active phospholipase, was considered to be the major toxin associated with NE. Alpha-toxin is composed of two domains, which are associated with phospholipase C activity (N-domain, 1-250 residues) and membrane recognition (C-domain, 251-370 residues), respectively. The C-terminal domain contributes to maintaining the active form of the toxin and mediates interactions with membrane phospholipids in a calcium-dependent manner. Individually these domains are non-toxic but immunogenic in mice resulting in the generation of antibody that reacts with the holotoxin, however, only immune responses against the C-domain provided protection against a subsequent challenge, possibly due to the blocking effects on the initial membrane-binding event. Therefore, the C-terminal domain of the alpha-toxin has been studied extensively as a vaccine against C. perfringens infection, delivered as a purified protein or by live attenuated bacteria. Currently the only commercially available vaccine for necrotic enteritis, Netvax®, is composed of an alpha toxoid derived from a C. perfringens type A strain.

Recent studies have identified a $\beta$-like toxin linked to necrotic enteritis, designated NetB toxin. It was identified in an Australian C. perfringens type A strain and has been proposed to be the most critical virulence factor for the development of NE in broilers. NetB is a pore-forming toxin encoded on a large conjugative plasmid (approximately 85 kb) within a 42 kilobase (kb) pathogenicity locus (NELoc-1), showing similarity to C. perfringens 0-toxin (38% identity). Several studies have screened for the presence of the netB gene within C. perfringens isolates and found that the presence of netB gene is highly correlated with necrotic enteritis strains. NetB is also a protective antigen, which could provide protection against C. perfringens challenge, especially in combination with other immunogenic components. Results consistent with a protective role for immune responses to NetB were obtained in a study that examined serum antibody levels against C. perfringens alpha-toxin and NetB toxin in commercial birds from field outbreaks of NE. The results showed that the levels of serum antibodies against both alpha-toxin and NetB toxin were significantly higher in apparently healthy chickens compared to birds with clinical signs of NE, suggesting that these antitoxin antibodies may play a role in protection against NE. Their results indicate a correlation between the presence of antitoxin antibodies in the serum and protective immunity against NE. In one study, purified $\alpha$-toxin C-fragment and NetB (W262A) toxoids were mixed (30 µg of each) in Quil A adjuvant and used to subcutaneously inject broiler birds 3 times, on days 3, 9 and 15. Birds injected with only one of the proteins were also included. The immunized birds were partially protected against a mild gavage challenge, but not against a more severe, in feed challenge. In some studies, hens were infected with NetB toxoid and antibodies against NetB were transferred from immunized hens to progeny, providing protection against *C. perfringens* challenge. In another study, immunization with both NetB and α-toxin toxoids using a live *Salmonella* delivery vector induced mucosal antibodies against both toxins and elicited a protective response. Strains engineered to deliver both toxoids provided significantly better protection than strains delivering each toxin alone.

In the current study, the immunogenicity of a novel PlcC-NetB fusion protein was examined in broiler birds.

Materials and Methods

Growth of *C. perfringens. C. perfringens* CP4 was cultured in cooked meat medium (CMM; Difco) and fluid thioglycollate medium (FTG; Difco).

Purification of PlcC, NetB and PlcC-NetB proteins. His-tagged PlcC (Zekarias, B., H. Mo, and R. Curtiss, III. 2008. Recombinant attenuated *Salmonella enterica* serovar *Typhimurium* expressing the carboxy-terminal domain of alpha toxin from *Clostridium perfringens* induces protective responses against necrotic enteritis in chickens. Clin Vaccine Immunol 15:805-816) and GST-NetB (Jiang, Y., H. Mo, C. Willingham, S. Wang, J. Y. Park, W. Kong, K. L. Roland, and R. Curtiss, 3rd. 2015. Protection Against Necrotic Enteritis in Broiler Chickens by Regulated Delayed Lysis *Salmonella* Vaccines. Avian diseases 59:475-485) proteins were prepared from *E. coli* as described.

A fusion protein PlcC-NetB was designed comprising the following components. The PlcC component represents aa 248-370 of alpha toxin (GenBank accession AAP15462.1) (SEQ ID NO: 3). The full-length, mature (i.e., after processing) Alpha toxin (GenBank accession AAP15462.1) is the following (SEQ ID NO: 16):

WDGKIDGTGTHAMIVTQGVSILENDMSKNEPESVRKNLEILKDNMHELQL

GSTYPDYDKNAYDLYQDHFWDPDTNNNFSKDNSWYLAYSIPDTGESQIRK

FSALARYEWQRGNYKQATFYLGEAMHYFGDIDTPYHPANVTAVDSAGHVK

FETFAEERKEQYKINTVGCKTNEDFYADILKNKDFNAWSKEYARGFAKTG

KSIYYSHASMSHSWDDWDYAAKVTLANSQKGTAGYIYRFLHDVSEGNDPS

VGNNVKELVAYISTSGEKDAGTDDYMYFGIKTKDGKTQEWEMDNPGNDFM

AGSKDTYTFKLKDENLKIDDIQNMWIRKRKYTAFPDAYKPENIKVIANGK

VVVDKDINEWISGNSTYNIK

The PlcC component, which is aa 248-370 of alpha toxin (GenBank accession AAP15462.1) (SEQ ID NO: 3) is the following:

DPSVGNNVKELVAYISTSGEKDAGTDDYMYFGIKTKDGKTQEWEMDNPGN

DFMAGSKDTYTFKLKDENLKIDDIQNMWIRKRKYTAFPDAYKPENIKVIA

NGKVVVDKDINEWISGNSTYNIK

The NetB component represents amino acids 31-322 of NetB (GenBank accession ACN73257.1) (SEQ ID NO: 5). The full-length NetB (GenBank accession ACN73257.1) is the following (SEQ ID NO: 17):

MKRLKIISITLVLTSVISTSLFSTQTQVFASELNDINKIELKNLSGEIIK

ENGKEAIKYTSSDTASHKGWKATLSGTFIEDPHSDKKTALLNLEGFIPSD

KQIFGSKYYGKMKWPETYRINVKSADVNNNIKIANSIPKNTIDKKDVSNS

IGYSIGGNISVEGKTAGAGINASYNVQNTISYEQPDFRTIQRKDDANLAS

WDIKFVETKDGYNIDSYHAIYGNQLFMKSRLYNNGDKNFTDDRDLSTLIS

GGFSPNMALALTAPKNAKESVIIVEYQRFDNDYILNWETTQWRGTNKLSS

TSEYNEFMFKINWQDHKIEYYL

The NetB component, which is amino acids 31-322 of NetB (GenBank accession ACN73257.1) (SEQ ID NO: 5) is the following:

SELNDINKIELKNLSGEIIKENGKEAIKYTSSDTASHKGWKATLSGTFIE

DPHSDKKTALLNLEGFIPSDKQIFGSKYYGKMKWPETYRINVKSADVNNN

IKIANSIPKNTIDKKDVSNSIGYSIGGNISVEGKTAGAGINASYNVQNTI

SYEQPDFRTIQRKDDANLASWDIKFVETKDGYNIDSYHAIYGNQLFMKSR

LYNNGDKNFTDDRDLSTLISGGFSPNMALALTAPKNAKESVIIVEYQRFD

NDYILNWETTQWRGTNKLSSTSEYNEFMFKINWQDHKIEYYL

Figure 2:
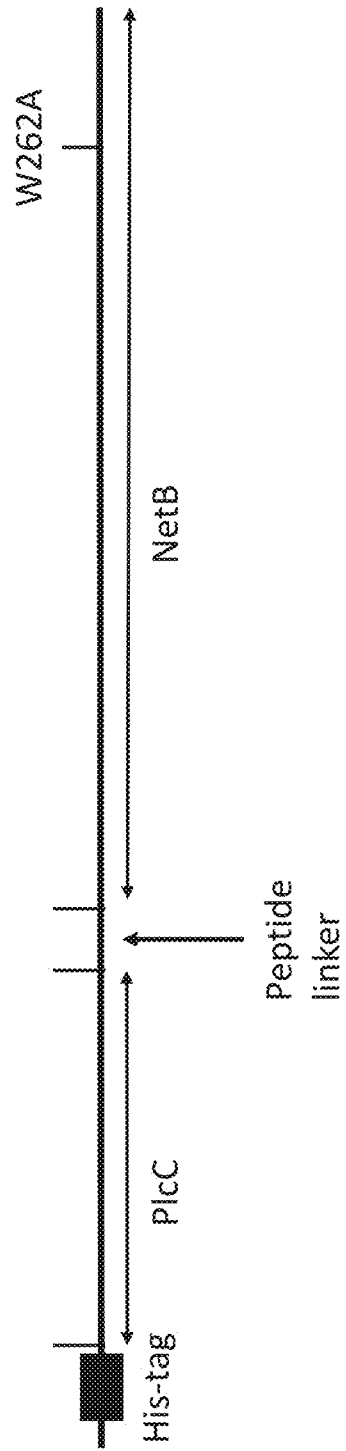

The PlcC component is linked to the NetB component by the peptide linker "GGSGGSGGPSGGSGG" (SEQ ID NO: 4), with NetB on the C-terminal side. A 6His tag (HHHHHHH, SEQ ID NO:2) and linker "HHHHHHGS" (SEQ ID NO: 15) is fused to the N-terminus of PlcC (FIG. 2). Because the toxins are naturally secreted in *C. perfringens* via a processed N-terminal signal peptide, we directed the expressed fusion protein to the endoplasmic reticulum (ER) of plant cells, reasoning that correct protein folding may be enhanced by the chaperones present in the ER. In order to target the fusion protein to the ER of plant cells, the plant signal peptide from barley alpha amylase "MANKHLSLSLFLVLLGLSASLASG" (SEQ ID NO:1) is fused to the N-terminus of the 6His tag. Examination of the sequence using SignalP 4.1 (http://www.cbs.dtu.dk/services/SignalP/) and selecting "Eukaryotes" indicates that signal peptidase cleavage is likely to occur between positions 24 and 25: ASG-HH.

A plant codon-optimized coding sequence was designed to enable high expression in a tobacco relative, *Nicotiana benthamiana*. Codons were selected that are more frequently used in highly expressed genes of tobacco and *Arabidopsis* (Geyer, B. C., L. Kannan, I. Cherni, R. R. Woods, H. Soreq, and T. S. Mor. 2010. Transgenic plants as a source for the bioscavenging enzyme, human butyrylcholinesterase. Plant Biotechnol J 8:873-886). Sequences were eliminated that could specify RNA processing (splicing, polyadenylation) or destabilization. A commercial service was used for gene synthesis and cloned the fragment via XbaI at 5' and SacI at 3' into an expression vector based on a bean yellow dwarf virus replicon, pBYR2eK2M (Diamos, A. G., S. H. Rosenthal, and H. S. Mason. 2016. 5' and 3' Untranslated Regions Strongly Enhance Performance of Geminiviral Replicons in *Nicotiana benthamiana* Leaves. Front Plant Sci 7:200). The resulting construct pBYR2eK2M-6HplcCnetB was verified by DNA sequencing and transformed into the disarmed *Agrobacterium tumefaciens* strain EHA105. Transient expression in leaves We performed by *Agrobacterium*-mediated DNA delivery. Briefly, *Agrobacterium* cells were grown overnight in LB media with 50 µg/ml kanamycin and 1 µg/ml rifampicin, and then cells were collected and resuspended in 10 mM 2-(N-morpholino)ethanesulfonic acid (MES), pH 5.5 and 10 mM $MgSO_4$ to $OD_{600}$=0.2. The resulting bacterial suspensions were injected into leaves through a small puncture using a syringe without needle (Huang, Z., and H. S. Mason. 2004. Conformational analysis of hepatitis B surface antigen fusions in an *Agrobacterium*-mediated transient expression system. Plant Biotechnol J 2:241-249). The plants were cultured in a growth room under moderate light at 25° C. for 4 days before leaves were harvested and weighed.

The leaves were extracted using a blender in 3-fold mass of buffer (phosphate buffered saline pH 7.5 (PBS), 50 mM sodium ascorbate, 1 mM phenylmethylsulfonyl fluoride, 0.1% Triton X-100), and insoluble debris was removed by centrifugation (10,000×g, 4° C., 15 min). The supernatant was collected and 1 M phosphoric acid was added while stirring at 4° C. until the pH=4.8, and then 1 M Tris base was added until the supernatant reached pH=7.5. Precipitated material was removed by centrifugation (10,000×g, 4° C., 15 min), and the supernatant containing recombinant PlcC-NetB was subjected to metal affinity chromatography, using Talon® affinity resin (http://www.clontech.com). Bound protein was eluted by washing the column with 150 mM imidazole, and fractions were assayed by absorbance at 280 nm. Combined fractions with the highest protein content were dialyzed against PBS, pH 7.5, and the $A_{280}$ was measured. Protein concentration was calculated using the theoretical extinction coefficient based on the amino acid sequence of the fusion protein.

The ER-targeted construct resulted in high expression and accumulation of soluble PlcC-NetB fusion protein, which was verified by western blotting using anti-PlcC and anti-NetB antisera (data not shown). The fusion antigen was readily purified using metal affinity chromatography.

Detection of Antibody Response by Enzyme-Linked Immunosorbent Assay (ELISA)

ELISAs were performed in triplicate as described (Jiang, Y., Q. Kong, K. L. Roland, and R. Curtiss, 3rd. 2014. Membrane vesicles of *Clostridium perfringens* type A strains induce innate and adaptive immunity. International journal of medical microbiology: IJMM 304:431-443) to determine the titer of IgY r against PlcC, NetB and PlcC-NetB in chicken sera. Nunc Immunoplate Maxisorb F96 plates (Nalge Nunc, Rochester, N.Y.) were coated overnight at 4° C. with purified proteins at 100 ng/well suspended in sodium carbonate-bicarbonate buffer (pH 9.6). The plates were blocked with Sea Block blocking buffer (Fisher). Sera from individual birds were serially diluted in 2-fold steps from an initial dilution of 1:10 in PBS, respectively. After 1 h incubation at 37° C., wells were washed three times with PBS-0.05% Tween-20. The plates were incubated with biotinylated IgY (Southern Biotech) antibodies diluted 1:10,000 for 1 h at 37° C. Then streptavidin horseradish peroxidase conjugate (Southern Biotech) was added at a 1:4,000 dilution. 2,2'-azino-bis-(3-ethylbenzthiazoline-6-sulfonic acid) (ABTS, KPL, Inc) was then added to develop the reaction. Color development (absorbance) was recorded at 405 nm using a SpectraMax M2 Multi-Mode Microplate Reader (Molecular Devices, LLC). Endpoint titers were expressed as the reciprocal log 2 values as the last sample dilution with an absorbance of 0.1 OD unit above that for the negative controls.

Chicken Experiments.

All animal experiments were conducted in compliance with the Arizona State University Institutional Animal Care and Use Committee and the Animal Welfare Act. Any chickens that had reached a pre-determined severity of clinical illness prior to the end of the experiment were humanely euthanized and necropsied. One-day-old Cornish×Rock broiler chickens were purchased from Murray McMurray Hatchery (Webster City, Iowa) and typically arrived at our facility at 2 days of age. Birds were randomly sorted and placed in pens with pine shavings on the floor. Food and water was supplied ad libitum.

Experiment 1. One week old broiler birds were vaccinated subcutaneously three times at weekly intervals with 50 µg of purified PlcC-NetB fusion protein plus 50 µg of Quil A as adjuvant. The first immunization was at 1 week of age. Control birds mock-vaccinated with Quil A only. The volume was 100 µl for all inoculations.

Experiment 2. Broiler birds were vaccinated subcutaneously three times at weekly intervals with 100 µg of purified PlcC-NetB fusion protein plus 50 µg of Quil A as adjuvant. Control birds mock-vaccinated with Quil A only. The volume was 100 µl for $1^{st}$ and $2^{nd}$ inoculations and 200 µl for $3^{rd}$ inoculation due to the lower concentration of protein in that preparation.

In Experiment 1, serum was taken one week after the final immunization and assayed for IgY antibodies against PlcC, NetB and PlcC-NetB fusion protein.

Challenge procedure. The in-feed challenge performed as described previously (Jiang, Y., H. Mo, C. Willingham, S. Wang, J. Y. Park, W. Kong, K. L. Roland, and R. Curtiss, 3rd. 2015. Protection Against Necrotic Enteritis in Broiler Chickens by Regulated Delayed Lysis *Salmonella* Vaccines. Avian diseases 59:475-485; Shojadoost, B., A. R. Vince, and J. F. Prescott. 2012. The successful experimental induction of necrotic enteritis in chickens by *Clostridium perfringens*: a critical review. Vet Res 43:74). Three weeks after the first immunization, birds were challenged in-feed for 5 days with *C. perfringens* CP4, a virulent strain isolated from a necrotic enteritis outbreak. The day after the final challenge birds were euthanized and necropsies performed. At necropsy, intestinal tracts were examined and scored for lesions typical of necrotic enteritis. The person performing the scoring was blinded to the treatment regimen each bird received. Intestinal lesions are scored as follows: 0=no gross lesions; 1=thin or friable wall or diffuse superficial but removable fibrin; 2=focal necrosis or ulceration, or non-removable fibrin deposit, 1 to 5 foci; 3=focal necrosis or ulceration, or non-removable fibrin deposit, 6 to 15 foci; 4=focal necrosis or ulceration, or non-removable fibrin deposit, 16 or more foci; 5=patches of necrosis 2 to 3 cm long; 6=diffuse necrosis typical of field cases.

Results

PlcC-NetB protein production in *Nicotiana benthamiana*. A codon-optimized gene was designed (FIG. 2) for expression of PlcC-NetB in *Nicotiana benthamiana*, and it was cloned in an expression vector based on a bean yellow dwarf virus replicon (Diamos, A. G., S. H. Rosenthal, and H. S. Mason. 2016. 5' and 3' Untranslated Regions Strongly Enhance Performance of Geminiviral Replicons in *Nicotiana benthamiana* Leaves. Front Plant Sci 7:200). The system uses transient expression in leaves, with amplified DNA and greatly enhanced protein expression only four days after *Agrobacterium*-mediated DNA delivery. Because the toxins are naturally secreted in *C. perfringens* via a processed N-terminal signal peptide, the expressed fusion protein was directed to the ER of plant cells using a barley alpha-amylase signal peptide, reasoning that correct protein folding may be enhanced by the chaperones present in the ER. The construct resulted in high expression and accumulation of soluble PlcC-NetB fusion protein, which was readily purified using metal affinity chromatography, and used for a preliminary chicken immunization experiment (see below). The data indicate that the plant-made fusion protein was immunogenic.

Figure 3:
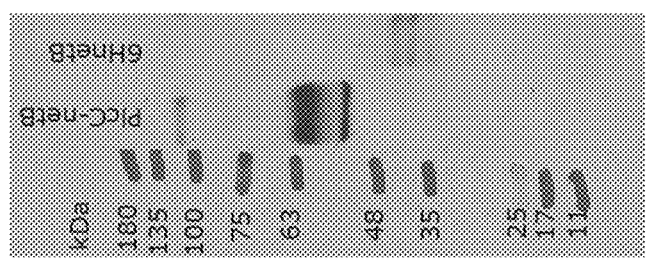

Evidence was observed on western blots that the PlcC-NetB accumulated in several glycosylated forms (FIG. 3). A search of the PlcC-NetB amino acid sequence for consensus Asn-linked glycosylation sites (Asn-X-Ser/Thr) showed one site in the PlcC and four sites in the NetB domain. Mapping of these sites on the 3-dimensional structures of Plc and NetB showed that they mostly occur in surface loops, and thus probably would not interfere with correct folding of the proteins or impair the antigen structure of protective epitopes. In some cases, such eukaryotic glycosylation was shown to be either neutral in effect or enhance immunogenicity of plant-made antigens (Boes, A., H. Spiegel, G. Edgue, S. Kapelski, M. Scheuermayer, R. Fendel, E. Remarque, F. Altmann, D. Maresch, A. Reimann, G. Pradel, S. Schillberg, and R. Fischer. 2015. Detailed functional characterization of glycosylated and nonglycosylated variants of malaria vaccine candidate PfAMA1 produced in Nicotiana benthamiana and analysis of growth inhibitory responses in rabbits. Plant Biotechnol J 13:222-234.; Joensuu, J. J., M. Kotiaho, T. H. Teeri, L. Valmu, A. M. Nuutila, K. M. Oksman-Caldentey, and V. Niklander-Teeri. 2006. Glycosylated F4 (K88) fimbrial adhesin FaeG expressed in barley endosperm induces ETEC-neutralizing antibodies in mice. Transgenic Res 15:359-373; Yuki, Y., M. Mejima, S. Kurokawa, T. Hiroiwa, Y. Takahashi, D. Tokuhara, T. Nochi, Y. Katakai, M. Kuroda, N. Takeyama, K. Kashima, M. Abe, Y. Chen, U. Nakanishi, T. Masumura, Y. Takeuchi, H. Kozuka-Hata, H. Shibata, M. Oyama, K. Tanaka, and H. Kiyono. 2013. Induction of toxin-specific neutralizing immunity by molecularly uniform rice-based oral cholera toxin B subunit vaccine without plant-associated sugar modification. Plant Biotechnol J 11:799-808). However, it is difficult to predict the effects of glycosylation on the immunogenicity of PlcC-NetB. Although the preliminary study showed it is immunogenic in chickens, it is possible that a non-glycosylated protein will be even more potent. Thus, a new expression vector was constructed that lacks the N-terminal signal sequence, which resulted in cytosolic accumulation and thus unglycosylated antigen. The glycosylated and unglycosylated antigens are used in further studies to test immunogenicity and protection in chickens.

Figures 4A, 4B, 4C:
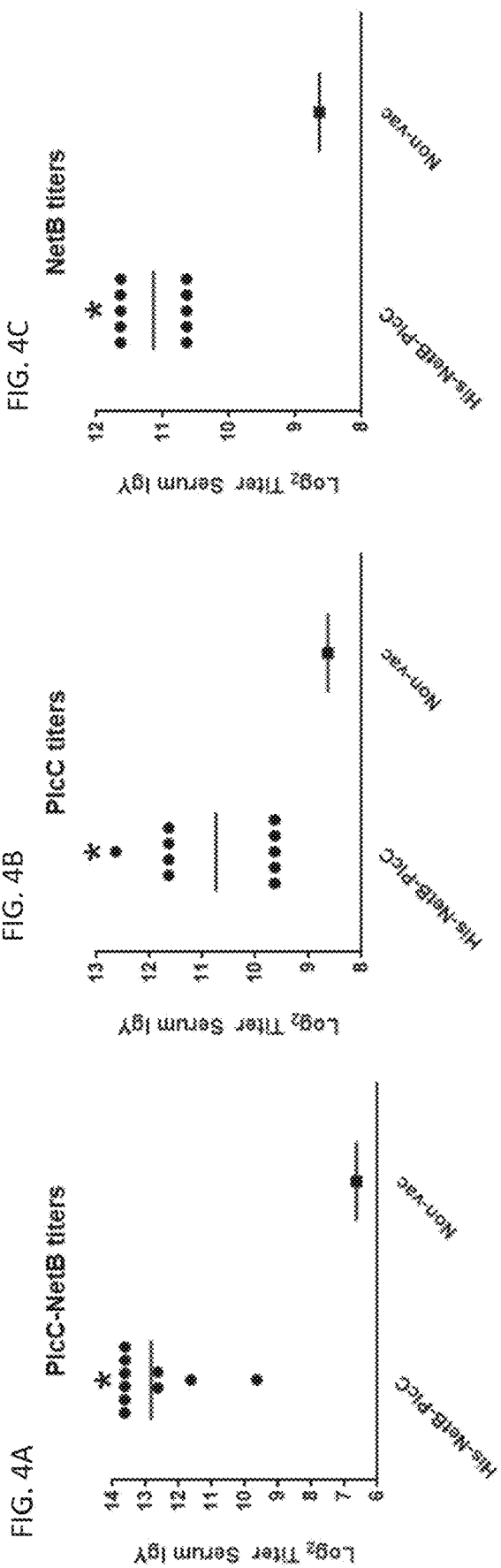
Figure 5:
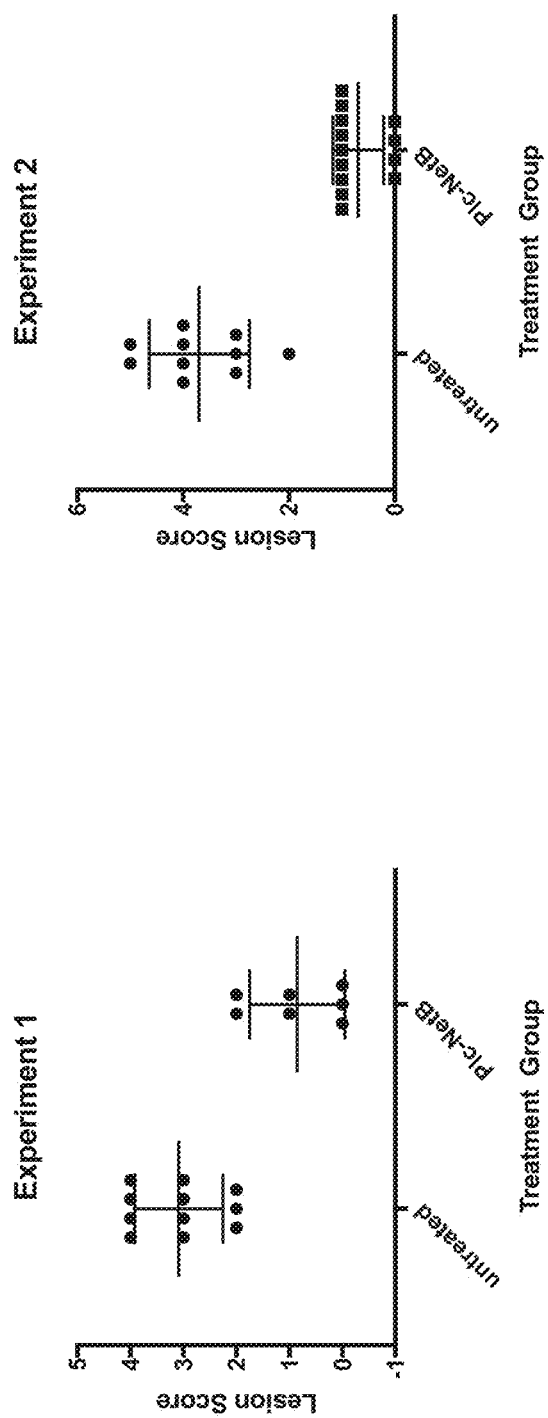

Serum antibody responses to the PlcC-NetB fusion protein. Serum IgY responses against the PlcC-NetB protein were significantly higher in immunized birds compared to non-vaccinated controls (FIG. 4A), indicating that PlcC-NetB is highly immunogenic. However, the protein is glycosylated (FIG. 3) and some of the reacting antibodies could be against the carbohydrate moieties, which are not present in the corresponding proteins produced by C. perfringens. To examine the responses against the proteinaceous epitopes, PlcC and NetB proteins purified from E. coli were used as the coating antigen. Although the titers were somewhat lower, they remained significantly higher than titers from control animals, indicating that protein epitopes in the PlcC (FIG. 4B) and NetB (FIG. 4C) were being recognized.

Protection Against C. perfringens Challenge.

The results from both challenge experiments are summarized below in Table 1 and graphically in FIG. 4. The challenge in Experiment 1 was milder than in Experiment 2, based on the fact that in Experiment 1, none of the birds in the control group received a lesion score of 5. This was due to the fact that different subclones of CP4 were used in each experiment. Interestingly, the vaccinated birds in Experiment 2 had overall healthier intestinal tracts than in Experiment 1. In Experiment 1 in which the birds received three doses of 50 μg of PlcC-NetB, after challenge, the intestines of most of the vaccinated birds displayed friability, even in the absence of fibrin. In Experiment 2, where the birds received three doses of 100 μg of PlcC-NetB, there was little friability and only scattered, removable fibrin. This is remarkable considering that the challenge was stronger in Experiment 2. These results demonstrate that the PlcC-NetB protein is highly immunogenic and protective against an in-feed challenge with a highly virulent C. perfringens strain.

TABLE 1

Lesion scores in immunized and non-immunized birds

| Group | Lesion Score | | | | | | | Average Lesion Score |
|---|---|---|---|---|---|---|---|---|
| | 0 | 1 | 2 | 3 | 4 | 5 | 6 | |
| Exp. 1 | | | | | | | | |
| PlcC-NetB | 3 | 2 | 2 | 0 | 0 | 0 | 0 | 0.9* |
| Mock | 0 | 0 | 3 | 4 | 3 | 0 | 0 | 3.0 |
| Exp. 2 | | | | | | | | |
| PlcC-NetB | 4 | 9 | 0 | 0 | 0 | 0 | 0 | 0.7* |
| Mock | 0 | 0 | 1 | 3 | 4 | 2 | 0 | 3.7 |

*Different from controls, P = 0.0004 by Mann-Whitney test
**Different from controls, P < 0.001 by Mann-Whitney test
Experiment 1: n = 7, PlcC-NetB group; n = 10, mock vaccinated group
Experiment 2: n = 13, PlcC-NetB group; n = 10, mock vaccinated group Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid encoding an antigenic protein comprising a PlcC protein unit that is operably linked to a peptide linker that is operably linked to a NetB protein unit, wherein the PlcC protein unit, the peptide linker and the NetB protein unit each have an N-terminus and a C-terminus, wherein the C-terminus of the PlcC protein unit is linked to the N-terminus of the peptide linker, wherein the C-terminus of the peptide linker is operably linked to the N-terminus of the NetB protein unit, and wherein the peptide linker has at least 95% sequence identity to SEQ ID NO: 4.

2. The nucleic acid of claim 1, wherein the PlcC protein unit has at least 95% sequence identity to SEQ ID NO: 3.

3. The nucleic acid of claim 1, wherein the NetB protein unit has at least 95% sequence identity to SEQ ID NO: 5.

4. The nucleic acid of claim 3, wherein the NetB protein unit has one or more amino acid substitutions at Y191A, R200A, W257A and W262A, S254L, R230Q or W287R of SEQ ID NO: 5.

5. The nucleic acid of claim 1, further comprising a 6Hist tag (SEQ ID NO: 2) having an N-terminus and a C-terminus, wherein the C-terminus of the 6Hist tag is operably linked to the N-terminus of the PlcC protein unit.

6. The nucleic acid of claim 5, further comprising a plant signal peptide having an N-terminus and a C-terminus, wherein the C-terminus of the plant signal peptide is operably linked to the N-terminus of the 6Hist tag, wherein the plant signal peptide has at least 95% sequence identity to SEQ ID NO: 1.

7. The nucleic acid of claim 1, wherein the nucleic acid has at least 95% sequence identity to SEQ ID NO: 6.

8. An expression cassette comprising the nucleic acid of claim 1 and a promoter, wherein the promoter is a plant promoter.

9. The expression cassette of claim 8, wherein the plant promoter is operable in corn or rice.

10. The expression cassette of claim 8, wherein the plant promoter is operable in seed tissue.

11. A recombinant vector comprising the expression cassette of claim 8 and a vector.

12. The recombinant vector of claim 11, wherein the vector is a bean yellow dwarf virus replicon.

13. A plant cell comprising the antigenic protein of claim 1.

14. The plant cell of claim 13, further comprising an *E. coli* heat-labile enterotoxin (LT) and/or a cholera toxin (CT).

15. Animal feed comprising the plant cell of claim 13.

* * * * *

SEQUENCE LISTING

<160> NUMBER OF SEQ ID NOS: 17

<210> SEQ ID NO 1
<211> LENGTH: 24
<212> TYPE: PRT
<213> ORGANISM: Unknown
<220> FEATURE:
<223> OTHER INFORMATION: Description of Unknown:
      Plant signal peptide

<400> SEQUENCE: 1

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 123
<212> TYPE: PRT
<213> ORGANISM: Clostridium perfringens

<400> SEQUENCE: 3

Asp Pro Ser Val Gly Asn Asn Val Lys Glu Leu Val Ala Tyr Ile Ser
1               5                   10                  15

Thr Ser Gly Glu Lys Asp Ala Gly Thr Asp Asp Tyr Met Tyr Phe Gly
            20                  25                  30

Ile Lys Thr Lys Asp Gly Lys Thr Gln Glu Trp Glu Met Asp Asn Pro
        35                  40                  45

Gly Asn Asp Phe Met Ala Gly Ser Lys Asp Thr Tyr Thr Phe Lys Leu
    50                  55                  60

Lys Asp Glu Asn Leu Lys Ile Asp Asp Ile Gln Asn Met Trp Ile Arg
65                  70                  75                  80

Lys Arg Lys Tyr Thr Ala Phe Pro Asp Ala Tyr Lys Pro Glu Asn Ile
                85                  90                  95

Lys Val Ile Ala Asn Gly Lys Val Val Val Asp Lys Asp Ile Asn Glu
            100                 105                 110

Trp Ile Ser Gly Asn Ser Thr Tyr Asn Ile Lys
        115                 120

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Gly Gly Ser Gly Gly Pro Ser Gly Gly Ser Gly Gly
1               5                   10                  15

<210> SEQ ID NO 5
<211> LENGTH: 292
<212> TYPE: PRT
<213> ORGANISM: Clostridium perfringens

<400> SEQUENCE: 5

```
Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
    290
```

<210> SEQ ID NO 6
<211> LENGTH: 1389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atggctaaca agcacctctc attgtctctc ttccttgtgc tccttggtct ttctgcttct      60
cttgcttctg gtcaccatca ccatcatcac ggatccgacc catccgtggg aaacaacgtt     120
```

```
aaggagcttg tggcttacat ctccacttct ggagagaagg acgctggaac cgacgattac    180
atgtacttcg gtatcaagac caaggatgga aagactcaag aatgggagat ggacaatcca    240
ggtaacgact tcatggctgg tagcaaggat acttacactt tcaagttgaa agacgagaac    300
cttaagatcg acgacatcca gaacatgtgg attaggaaac gtaagtacac cgccttccca    360
gacgcttaca agcctgagaa catcaaggtt atcgctaacg gaaaggtggt tgttgacaag    420
gatatcaacg agtggatttc tggaaactcc acttacaaca tcaaaggagg ttctggtgga    480
tcaggaggtc catctggagg ttctggagga tccgagctta cgacatcaa caagattgag    540 cttaagaacc tctccggaga gatcatcaag gagaacggta aggaggctat caagtacact    600
tcttccgaca ccgcttccca aagggatgg aaggccactc tttctggaac cttcatcgaa    660
gaccctcatt ctgacaagaa gactgctttg cttaaccttg aaggattcat cccatctgac    720
aaacagatct tcggatctaa gtactacgga aagatgaagt ggcctgagac ttacaggatc    780
aacgtgaaga gcgctgacgt taacaacaac atcaagatcg ccaactctat tccgaagaac    840
actatcgaca agaaggacgt gtccaattct atcggttact ccatcggagg taacatctct    900
gttgagggta agactgctgg tgctggaatc aacgcttctt acaacgttca gaacactatc    960
tcctatgagc aacctgactt cagaaccatt cagaggaagg acgatgctaa ccttgcatcc   1020
tgggacatca aattcgttga gactaaggac ggatacaaca tcgactccta ccatgctatc   1080
tatggcaacc agctcttcat gaagagcaga ttgtacaaca atggtgacaa gaacttcacc   1140
gacgataggg acctctccac cttgatctct ggtggattct ctccaaacat ggctcttgcc   1200
ttgaccgctc ctaagaacgc taaggagtca gtgatcatcg ttgaatacca gaggttcgac   1260
aacgactata tccttaactg ggagactact caagctagag gaactaacaa gctttcttca   1320
acctccgagt acaacgagtt tatgttcaag atcaactggc aggaccacaa gatcgaatac   1380
tatctttaa                                                           1389
```

<210> SEQ ID NO 7
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atggctaaca agcacctctc attgtctctc ttccttgtgc tccttggtct ttctgcttct     60
cttgcttctg gtcaccatca ccatcatcac ggatccgacc catccgtggg aaacaacgtt    120
aaggagcttg tggcttacat ctccacttct ggagagaagg acgctggaac cgacgattac    180
atgtacttcg gtatcaagac caaggatgga aagactcaag aatgggagat ggacaatcca    240
ggtaacgact tcatggctgg tagcaaggat acttacactt tcaagttgaa agacgagaac    300
cttaagatcg acgacatcca gaacatgtgg attaggaaac gtaagtacac cgccttccca    360
gacgcttaca agcctgagaa catcaaggtt atcgctaacg gaaaggtggt tgttgacaag    420
gatatcaacg agtggatttc tggaaactcc acttacaaca tcaaaggagg ttctggtgga    480
tcaggaggtc catctggagg ttctggagga tccgagctta cgacatcaa caagattgag    540 cttaagaacc tctccggaga gatcatcaag gagaacggta aggaggctat caagtacact    600
tcttccgaca ccgcttccca aagggatgg aaggccactc tttctggaac cttcatcgaa    660
gaccctcatt ctgacaagaa gactgctttg cttaaccttg aaggattcat cccatctgac    720
```

```
aaacagatct tcggatctaa gtactacgga agatgaagt  ggcctgagac ttacaggatc      780
aacgtgaaga gcgctgacgt taacaacaac atcaagatcg ccaactctat tccgaagaac      840
actatcgaca agaaggacgt gtccaattct atcggttact ccatcggagg taacatctct      900
gttgagggta agactgctgg tgctggaatc aacgcttctt acaacgttca gaacactatc      960
tcctatgagc aacctgactt cagaaccatt cagaggaagg acgatgctaa ccttgcatcc     1020
tgggacatca aattcgttga gactaaggac ggatacaaca tcgactccta ccatgctatc     1080
tatggcaacc agctcttcat gaagagcaga ttgtacaaca atggtgacaa gaacttcacc     1140
gacgataggg acctctccac cttgatctct ggtggattct ctccaaacat ggctcttgcc     1200
ttgaccgctc ctaagaacgc taaggagtca gtgatcatcg ttgaatacca gaggttcgac     1260
aacgactata tccttaactg ggagactact caagctagag gaactaacaa gcttcttca      1320 acctccgagt acaacgagtt tatgttcaag atcaactggc aggaccacaa gatcgaatac     1380
tatctt                                                                1386
```

<210> SEQ ID NO 8
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atggctcacc atcaccatca tcacggatcc gacccatccg tgggaaacaa cgttaaggag       60
cttgtggctt acatctccac ttctggagag aaggacgctg gaaccgacga ttacatgtac      120
ttcggtatca agaccaagga tggaaagact caagaatggg agatggacaa tccaggtaac      180
gacttcatgg ctggtagcaa ggatacttac actttcaagt tgaaagacga gaaccttaag      240
atcgacgaca tccagaacat gtggattagg aaacgtaagt acaccgcctt cccagacgct      300
tacaagcctg agaacatcaa ggttatcgct aacggaaagg tggttgttga caaggatatc      360
aacgagtgga tttctggaaa ctccacttac aacatcaaag gaggttctgg tggatcagga      420
ggtccatctg gaggttctgg aggatccgag cttaacgaca tcaacaagat tgagcttaag      480
aacctctccg agagatcat  caaggagaac ggtaaggagg ctatcaagta cacttcttcc      540
gacaccgctt cccacaaggg atggaaggcc actctttctg gaaccttcat cgaagaccct      600
cattctgaca agaagactgc tttgcttaac cttgaaggat tcatcccatc tgacaaacag      660
atcttcggat ctaagtacta cggaaagatg aagtggcctg agacttacag gatcaacgtg      720
aagagcgctg acgttaacaa caacatcaag atcgccaact ctattccgaa gaacactatc      780
gacaagaagg acgtgtccaa ttctatcggt tactccatcg gaggtaacat ctctgttgag      840
ggtaagactc tggtgctgg  aatcaacgct tcttacaacg ttcagaacac tatctcctat      900
gagcaacctg acttcagaac cattcagagg aaggacgatg ctaaccttgc atcctgggac      960
atcaaattcg ttgagactaa ggacggatac aacatcgact cctaccatgc tatctatggc     1020
aaccagctct tcatgaagag cagattgtac aacaatggtg acaagaactt caccgacgat     1080
agggacctct ccaccttgat ctctggtgga ttctctccaa acatggctct tgccttgacc     1140
gctcctaaga acgctaagga gtcagtgatc atcgttgaat accagaggtt cgacaacgac     1200
tatatcctta actgggagac tactcaagct agaggaacta acaagctttc ttcaacctcc     1260
gagtacaacg agtttatgtt caagatcaac tggcaggacc acaagatcga atactatctt     1320
```

<210> SEQ ID NO 9
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggctaaca agcacctctc attgtctctc ttccttgtgc tccttggtct ttctgcttct    60
cttgcttctg gtcaccatca ccatcatcac ggatccgacc catccgtggg aaacaacgtt   120
aaggagcttg tggcttacat ctccacttct ggagagaagg acgctggaac cgacgattac   180
atgtacttcg gtatcaagac caaggatgga aagactcaag aatgggagat ggacaatcca   240
ggtaacgact tcatggctgg tagcaaggat acttacactt tcaagttgaa agacgagaac   300
cttaagatcg acgacatcca gaacatgtgg attaggaaac gtaagtacac cgccttccca   360
gacgcttaca agcctgagaa catcaaggtt atcgctaacg gaaaggtggt tgttgacaag   420
gatatcaacg agtggatttc tggaaactcc acttacaaca tcaaa                  465

<210> SEQ ID NO 10
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggctcacc atcaccatca tcacggatcc gacccatccg tgggaaacaa cgttaaggag    60
cttgtggctt acatctccac ttctggagag aaggacgctg gaaccgacga ttacatgtac   120
ttcggtatca agaccaagga tggaaagact caagaatggg agatggacaa tccaggtaac   180
gacttcatgg ctggtagcaa ggatacttac actttcaagt tgaaagacga gaaccttaag   240
atcgacgaca tccagaacat gtggattagg aaacgtaagt acaccgcctt cccagacgct   300
tacaagcctg agaacatcaa ggttatcgct aacggaaagg tggttgttga caaggatatc   360
aacgagtgga tttctggaaa ctccacttac aacatcaaa                         399

<210> SEQ ID NO 11
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggctaaca agcacctctc attgtctctc ttccttgtgc tccttggtct ttctgcttct    60
cttgcttctg gtcaccatca ccatcatcac ggatccgagc ttaacgacat caacaagatt   120
gagcttaaga acctctccgg agagatcatc aaggagaacg gtaaggaggc tatcaagtac   180
acttcttccg caccgcttc ccacaaggga tggaaggcca ctctttctgg aaccttcatc   240
gaagaccctc attctgacaa agagactgct tgcttaacc ttgaaggatt catcccatct   300
gacaaacaga tcttcggatc taagtactac ggaaagatga gtggcctga cttacagg     360 atcaacgtga gagcgctga cgttaacaac aacatcaaga tcgccaactc tattccgaag   420
aacactatcg acaagaagga cgtgtccaat tctatcggtt actccatcgg aggtaacatc   480

```
tctgttgagg gtaagactgc tggtgctgga atcaacgctt cttacaacgt tcagaacact    540
atctcctatg agcaacctga cttcagaacc attcagagga aggacgatgc taaccttgca    600
tcctgggaca tcaaattcgt tgagactaag gacggataca acatcgactc ctaccatgct    660
atctatggca accagctctt catgaagagc agattgtaca caatggtga caagaacttc    720 accgacgata gggacctctc caccttgatc tctggtggat ctctccaaa catggctctt    780 gccttgaccg ctcctaagaa cgctaaggag tcagtgatca tcgttgaata ccagaggttc    840
gacaacgact atatccttaa ctgggagact actcaagcta gaggaactaa caagctttct    900
tcaacctccg agtacaacga gtttatgttc aagatcaact ggcaggacca caagatcgaa    960
tactatctt                                                            969

<210> SEQ ID NO 12
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggctcacc atcaccatca tcacggatcc gagcttaacg acatcaacaa gattgagctt     60
aagaacctct ccggagagat catcaaggag aacggtaagg aggctatcaa gtacacttct    120
tccgacaccg cttcccacaa gggatggaag ccactctttc tggaaccttc atcgaagac    180 cctcattctg acaagaagac tgctttgctt aaccttgaag gattcatccc atctgacaaa    240
cagatcttcg gatctaagta ctacggaaag atgaagtggc ctgagactta caggatcaac    300
gtgaagagcg ctgacgttaa caacaacatc aagatcgcca actctattcc gaagaacact    360
atcgacaaga aggacgtgtc caattctatc ggttactcca tcggaggtaa catctctgtt    420
gagggtaaga ctgctggtgc tggaatcaac gcttcttaca acgttcagaa cactatctcc    480
tatgagcaac ctgacttcag aaccattcag aggaaggacg atgctaacct tgcatcctgg    540
gacatcaaat tcgttgagac taaggacgga tacaacatcg actcctacca tgctatctat    600
ggcaaccagc tcttcatgaa gagcagattg tacaacaatg gtgacaagaa cttcaccgac    660
gatagggacc tctccacctt gatctctggt ggattctctc aaacatggc tcttgccttg    720 accgctccta agaacgctaa ggagtcagtg atcatcgttg aataccagag gttcgacaac    780
gactatatcc ttaactggga gactactcaa gctagaggaa ctaacaagct tcttcaacc    840 tccgagtaca acgagtttat gttcaagatc aactggcagg accacaagat cgaatactat    900
ctt                                                                  903

<210> SEQ ID NO 13
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Asn Lys His Leu Ser Leu Ser Leu Phe Leu Val Leu Leu Gly
1               5                   10                  15

Leu Ser Ala Ser Leu Ala Ser Gly His His His His His Gly Ser
            20                  25                  30
```

-continued

Asp Pro Ser Val Gly Asn Asn Val Lys Glu Leu Val Ala Tyr Ile Ser
      35                  40                  45

Thr Ser Gly Glu Lys Asp Ala Gly Thr Asp Asp Tyr Met Tyr Phe Gly
      50                  55                  60

Ile Lys Thr Lys Asp Gly Lys Thr Gln Glu Trp Glu Met Asp Asn Pro
65                  70                  75                  80

Gly Asn Asp Phe Met Ala Gly Ser Lys Asp Thr Tyr Thr Phe Lys Leu
                  85                  90                  95

Lys Asp Glu Asn Leu Lys Ile Asp Asp Ile Gln Asn Met Trp Ile Arg
              100                 105                 110

Lys Arg Lys Tyr Thr Ala Phe Pro Asp Ala Tyr Lys Pro Glu Asn Ile
              115                 120                 125

Lys Val Ile Ala Asn Gly Lys Val Val Asp Lys Asp Ile Asn Glu
              130                 135                 140

Trp Ile Ser Gly Asn Ser Thr Tyr Asn Ile Lys Gly Gly Ser Gly Gly
145                 150                 155                 160

Ser Gly Gly Pro Ser Gly Gly Ser Gly Gly Ser Glu Leu Asn Asp Ile
                  165                 170                 175

Asn Lys Ile Glu Leu Lys Asn Leu Ser Gly Glu Ile Ile Lys Glu Asn
              180                 185                 190

Gly Lys Glu Ala Ile Lys Tyr Thr Ser Ser Asp Thr Ala Ser His Lys
              195                 200                 205

Gly Trp Lys Ala Thr Leu Ser Gly Thr Phe Ile Glu Asp Pro His Ser
              210                 215                 220

Asp Lys Lys Thr Ala Leu Leu Asn Leu Glu Gly Phe Ile Pro Ser Asp
225                 230                 235                 240

Lys Gln Ile Phe Gly Ser Lys Tyr Tyr Gly Lys Met Lys Trp Pro Glu
                  245                 250                 255

Thr Tyr Arg Ile Asn Val Lys Ser Ala Asp Val Asn Asn Ile Lys
              260                 265                 270

Ile Ala Asn Ser Ile Pro Lys Asn Thr Ile Asp Lys Lys Asp Val Ser
              275                 280                 285

Asn Ser Ile Gly Tyr Ser Ile Gly Gly Asn Ile Ser Val Glu Gly Lys
              290                 295                 300

Thr Ala Gly Ala Gly Ile Asn Ala Ser Tyr Asn Val Gln Asn Thr Ile
305                 310                 315                 320

Ser Tyr Glu Gln Pro Asp Phe Arg Thr Ile Gln Arg Lys Asp Asp Ala
                  325                 330                 335

Asn Leu Ala Ser Trp Asp Ile Lys Phe Val Glu Thr Lys Asp Gly Tyr
              340                 345                 350

Asn Ile Asp Ser Tyr His Ala Ile Tyr Gly Asn Gln Leu Phe Met Lys
              355                 360                 365

Ser Arg Leu Tyr Asn Asn Gly Asp Lys Asn Phe Thr Asp Asp Arg Asp
              370                 375                 380

Leu Ser Thr Leu Ile Ser Gly Gly Phe Ser Pro Asn Met Ala Leu Ala
385                 390                 395                 400

Leu Thr Ala Pro Lys Asn Ala Lys Glu Ser Val Ile Ile Val Glu Tyr
                  405                 410                 415

Gln Arg Phe Asp Asn Asp Tyr Ile Leu Asn Trp Glu Thr Thr Gln Ala
              420                 425                 430

Arg Gly Thr Asn Lys Leu Ser Ser Thr Ser Glu Tyr Asn Glu Phe Met
              435                 440                 445

Phe Lys Ile Asn Trp Gln Asp His Lys Ile Glu Tyr Tyr Leu 450          455         460

<210> SEQ ID NO 14
<211> LENGTH: 14282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | | | | | |
|---|---|---|---|---|---|
| cgatcggtcg | attcatagaa | gattagattt | ttcatagtat | ttttttaaag | taaaccttta   60 |
| actacggtta | ggacactttt | aagttaaatt | taatttgaac | ccttaaatta | attttttaaaa  120 |
| tagataaata | tcaatcatcc | tgatatgctt | ttgaaaaaat | gaatgagaaa | gatgattcaa  180 |
| ttaaggccac | attttaatca | tgactaaaat | aatatacagt | ataatttcat | atatatttgc  240 |
| tttaaaaaaa | aattgacaat | ccattcgttt | ctagcaataa | atttcttcaa | ccacaaatat  300 |
| attaaagata | actacggcat | agaaacaaaa | atctatgaag | aattttgta  | tacttcatat  360 |
| gaaattaaaa | aaaacttcat | tgaacatcaa | aataataata | ataatcataa | actcctcaat  420 |
| atttatattc | ctagcttctt | gaattaaatt | gtttacatat | tcaacgatgt | aaaaaattat  480 |
| ttctctatct | attttcctta | tatcatgcat | ggtttcacat | atatcaaagg | ataaaagcaa  540 |
| tctatgtaaa | ttatctcact | ttattaagtt | ttctatctga | attattgaga | acgtagattt  600 |
| ctttttgcac | tatcccccaa | taattagcaa | aacacaccta | gactagattt | gttttgctaa  660 |
| cccaattgat | attaattata | tatgattaat | atttatatgt | atatggaatt | ggttaataaa  720 |
| atgcatctgg | ttcatcaaag | aattataaag | acacgtgaca | ttcatttagg | ataagaaata  780 |
| tggatgatct | ctttctctta | ttcagataat | tagtaattac | acataacaca | caactttgat  840 |
| gcccacatta | tagtgattag | catgtcacta | tgtgtgcatc | cttttatttc | atacattaat  900 |
| taacttggcc | aatccagaag | atggacaagt | ctagggtcac | attgcagggt | actctagctt  960 |
| actcgccttc | ttttcgaag  | gtttgagtac | cttcagggca | tcctcttgat | acattacttt  1020 |
| ccacttcgat | tggggcaagc | tgtagcagtt | cttgcttaga | ccgaattgcc | atctcacaga  1080 |
| gatgctgaag | agttcgcgac | cctccagaaa | cggtgatact | aactcctcga | aaccgaatac  1140 |
| tataggtaca | tccgatctgg | tcgaaaccga | aaaatcgaga | tgctgcatag | ttaaccgaat  1200 |
| ctcccgtcca | agatccaagg | actctgtgca | gtgaagcttc | cgtcctgtcg | tatctgagat  1260 |
| atctcttaaa | tacaactttc | ccgaaacccc | agctttcctt | gaaaccaagg | ggattatctt  1320 |
| gattcgaatt | cgtctcatcg | ttatgtagcc | gccactcagt | ccaactcgga | ctttcgtcag  1380 |
| gaagtttgaa | gggagaagtt | gtacctcctg | atcctccatc | ccaacgttca | ctgttagctt  1440 |
| gttccctagc | gtcgtttcct | tgtatagctc | gttccatgga | ttgtaaatag | taattgtaat  1500 |
| gttgtttgtt | gtttgttgtt | gttggtaatt | gttgtaaaaa | tacgctctcc | aaatgaaatg  1560 |
| aacttcctta | tatagaggaa | gggtcttgcg | aaggatagtg | ggattgtgcg | tcatccctta  1620 |
| cgtcagtgga | gatatcacat | caatccactt | gctttgaaga | cgtggttgga | acgtcttctt  1680 |
| tttccacgat | gctcctcgtg | ggtggggtc  | catcttgggg | accactgtcg | gcagaggcat  1740 |
| cttcaacgat | ggccttttcct | ttatcgcaat | gatggcattt | gtaggagcca | ccttcctttt  1800 |
| ccactatctt | cacaataaag | tgacagatag | ctgggcaatg | gaatccgagg | aggtttccgg  1860 |
| atattaccct | ttgttgaaaa | gtctcaattg | ccctttggtc | ttctgagact | gtatctttga  1920 |
| tattttttgga | gtagacaagt | gtgtcgtgct | ccaccatgtt | ctggcaattc | cggttcgctt  1980 |

```
gctgtccata aaaccgccca gtctagctat cgccatgtaa gcccactgca agctacctgc    2040
tttctctttg cgcttgcgtt ttcccttgtc cagatagccc agtagctgac attcatccgg    2100
ggtcagcacc gtttctgcgg actggctttc tacgtgttcc gcttccttta gcagcccttg    2160
cgccctgagt gcttgcggca gcgtgaagct ggcgcgccgc tctagcagaa ggcatgttgt    2220
tgtgactccg aggggttgcc tcaaactcta tcttataacc ggcgtggagg catggaggca    2280
agggcatttt ggtaatttaa gtagttagtg gaaaatgacg tcatttactt aaagacgaag    2340
tcttgcgaca aggggggccc acgccgaatt ttaatattac cggcgtggcc ccaccttatc    2400
gcgagtgctt tagcacgagc ggtccagatt taaagtagaa aagttcccgc ccactagggt    2460
taaaggtgtt cacactataa aagcatatac gatgtgatgg tatttgataa agcgtatatt    2520
gtatcaggta tttccgtcgg atacgaatta ttcgtacgac cctcctgcag gtcaacatgg    2580
tggagcacga cacacttgtc tactccaaaa atatcaaaga tacagtctca gaagaccaaa    2640
gggcaattga dacttttcaa caaagggtaa tatccggaaa cctcctcgga ttccattgcc    2700
cagctatctg tcactttatt gtgaagatag tggaaaagga aggtggctcc tacaaatgcc    2760
atcattgcga taaaggaaag gccatcgttg aagatgcctc tgccgacagt ggtcccaaag    2820
atggaccccc acccacgagg agcatcgtgg aaaaagaaga cgttccaacc acgtcttcaa    2880
agcaagtgga ttgatgtgat aacatggtgg agcacgacac acttgtctac tccaaaaata    2940
tcaaagatac agtctcagaa gaccaaaggg caattgagac ttttcaacaa agggtaatat    3000
ccggaaacct cctcggattc cattgcccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg daccccacc cacgaggagc atcgtggaaa    3180
aagaagacgt tccaaccacg tcttcaaagc aagtggattg atgtgatatc tccactgacg    3240
taagggatga cgcacaatcc cactatcctt cgcaagaccc ttcctctata taggaagtt    3300 catttcattt ggagaggacc tcgagaaaca aacaaaatca acaaatatag aaaataacgc    3360
atttccaatt cttгgaaatt tctgcaacat ctagaacaat ggctaacaag cacctctcat    3420
tgtctctctt ccttgtgctc cttggtcttt ctgcttctct tgcttctggt caccatcacc    3480
atcatcacgg atccgaccca tccgtgggaa acaacgttaa ggagcttgtg cttacatct    3540 ccacttctgg agagaaggac gctggaaccg acgattacat gtacttcggt atcaagacca    3600
aggatggaaa gactcaagaa tgggagatgg acaatccagg taacgacttc atggctggta    3660
gcaaggatac ttacactttc aagttgaaag acgagaacct aagatcgac gacatccaga    3720 acatgtggat taggaaacgt aagtacaccg ccttcccaga cgcttacaag cctgagaaca    3780
tcaaggttat cgctaacgga aaggtggttg ttgacaagga tatcaacgag tggatttctg    3840
gaaactccac ttacaacatc aaaggaggtt ctggtggatc aggaggtcca tctggaggtt    3900
ctggaggatc cgagcttaac gacatcaaca gattgagct taagaacctc tccgagaga    3960 tcatcaagga gaacggtaag gaggctatca agtacacttc ttccgacacc gcttcccaca    4020
agggatggaa ggccactctt tctggaacct tcatcgaaga ccctcattct gacaagaaga    4080
ctgctttgct taaccttgaa ggattcatcc catctgacaa acagatcttc ggatctaagt    4140
actacggaaa gatgaagtgg cctgagactt acaggatcaa cgtgaagagc gctgacgtta    4200
acaacaacat caagatcgcc aactctattc gaagaacac tatcgacaag aaggacgtgt    4260
ccaattctat cggttactcc atcggaggta acatctctgt tgagggtaag actgctggtg    4320
ctggaatcaa cgcttcttac aacgttcaga acactatctc ctatgagcaa cctgacttca    4380
```

```
gaaccattca gaggaaggac gatgctaacc ttgcatcctg ggacatcaaa ttcgttgaga   4440
ctaaggacgg atacaacatc gactcctacc atgctatcta tggcaaccag ctcttcatga   4500
agagcagatt gtacaacaat ggtgacaaga acttcaccga cgatagggac ctctccacct   4560
tgatctctgg tggattctct ccaaacatgg ctcttgcctt gaccgctcct aagaacgcta   4620
aggagtcagt gatcatcgtt gaataccaga ggttcgacaa cgactatatc cttaactggg   4680
agactactca agctagagga actaacaagc tttcttcaac ctccgagtac aacgagttta   4740
tgttcaagat caactggcag gaccacaaga tcgaatacta tctttaagag ctcgaagtga   4800
catcacaaag ttgaaggtaa taaagccaaa ttaattaaga cattttcata atgatgtcaa   4860
gaatgcaaag caaattgcat aactgccttt atgcaaaaca ttaatataat ataaattata   4920
aagaactgcg ctctctgctt cttatttttct tagcttcatt tattagtcac tagctgttca   4980
gaattttcag tatcttttga tattactaag aacctaatca cacaatgtat attcttatgc   5040
aggaaaagca gaatgctgag ctaaaagaaa ggcttttttcc attttcgaga gacaatgaga   5100
aaagaagaag aagaagaaga agaagaagaa gaagaaaaga gtaaataata aagccccaca   5160
ggaggcgaag ttcttgtagc tccatgttat ctaagttatt gatattgttt gccctatatt   5220
ttatttctgt cattgtgtat gttttgttca gtttcgatct ccttgcaaaa tgcagagatt   5280
atgagatgaa taaactaagt tatattatta tacgtgttaa tattctcctc ctctctctag   5340 ctagccttttt gttttctctt tttcttattt gattttcttt aaatcaatcc attttaggag   5400
agggccaggg agtgatccag caaaacatga agattagaag aaacttccct ctttttttttc   5460 ctgaaaacaa tttaacgtcg agatttatct cttttttgtaa tggaatcatt tctacagtta   5520
tgacgaattc tcgattaaaa atcccaatta tatttggtct aatttagttt ggtattgagt   5580
aaaacaaatt cgaaccaaac caaatataa atatatagtt tttatatata tgcctttaag   5640 acttttttata gaattttctt taaaaaatat ctagaaatat ttgcgactct tctggcatgt   5700
aatatttcgt taaatatgaa gtgctccatt tttattaact ttaaataatt ggttgtacga   5760
tcactttctt atcaagtgtt actaaaatgc gtcaatctct ttgttcttcc atattcatat   5820
gtcaaaatct atcaaaattc ttatatatct ttttcgaatt tgaagtgaaa tttcgataat   5880
ttaaaattaa atagaacata tcattattta ggtatcatat tgattttttat acttaattac   5940 taaatttggt taacttttgaa agtgtacatc aacgaaaaat tagtcaaacg actaaaataa   6000
ataaatatca tgtgttatta agaaaattct cctataagaa tattttaata gatcatatgt   6060
ttgtaaaaaa aattaatttt tactaacaca tatatttact tatcaaaaat ttgacaaagt   6120
aagattaaaa taatattcat ctaacaaaaa aaaaaccaga aaatgctgaa aacccggcaa   6180
aaccgaacca atccaaaccg atatagttgg tttggtttga ttttgatata aaccgaacca   6240
actcggtcca tttgcacccc taatcataat agctttaata tttcaagata ttattaagtt   6300
aacgttgtca atatcctgga aattttgcaa aatgaatcaa gcctatatgg ctgtaatatg   6360
aatttaaaag cagctcgatg tggtggtaat atgtaattta cttgattcta aaaaaatatc   6420
ccaagtatta ataatttctg ctaggaagaa ggttagctac gatttacagc aaagccagaa   6480
tacaaagaac cataaagtga ttgaagctcg aaatatacga aggaacaaat atttttaaaa   6540
aaatacgcaa tgacttggaa caaaagaaag tgatatattt tttgttctta acaagcatc   6600 ccctctaaag aatggcagtt ttcctttgca tgtaactatt atgctcccctt cgttacaaaa   6660 attttggact actattggga acttcttctg aaaatagtgg taccgagtgt acttcaagtc   6720
```

```
agttggaaat caataaaatg attattttat gaatatattt cattgtgcaa gtagatagaa      6780
attacatatg ttacataaca cacgaaataa acaaaaaaac acaatccaaa acaaacaccc      6840
caaacaaaat aacactatat atatcctcgt atgaggagag gcacgttcag tgactcgacg      6900
attcccgagc aaaaaaagtc tccccgtcac acatatagtg ggtgacgcaa ttatcttcaa      6960
agtaatcctt ctgttgactt gtcattgata acatccagtc ttcgtcagga ttgcaaagaa      7020
ttatagaagg gatcccacct tttattttct tcttttttcc atatttaggg ttgacagtga      7080
aatcagactg gcaacctatt aattgcttcc acaatgggac gaacttgaag gggatgtcgt      7140
cgatgatatt ataggtggcg tgttcatcgt agttggtgaa gtcgatggtc ccgttccagt      7200
agttgtgtcg cccgagactt ctagcccagg tggtctttcc ggtacgagtt ggtccgcaga      7260
tgtagaggct ggggtgtctg accccagtcc ttccctcatc ctggttagat cggccatcca      7320
ctcaaggtca gattgtgctt gatcgtagga gacaggatgt atgaaagtgt aggcatcgat      7380
gcttacatga tataggtgcg tctctctcca gttgtgcaga tcttcgtggc agcggagatc      7440
tgattctgtg aagggcgaca cgtactgctc aggttgtgga ggaaataatt tgttggctga      7500
atattccagc cattgaagct tgttgcccca ttcatgaggg aactcttctt tgatcatgtc      7560
aagatactcc tccttagacg ttgcagtctg gataatagtt cgccatcgtg cgtcagattt      7620
gcgaggagac accttatgat ctcggaaatc tcctctggtt ttaatatctc cgtcctttga      7680
tatgtaatca aggacttgtt tagagtttct agctggctgg atattagggt gatttccttc      7740
aaaatcgaaa aaagaaggat ccctaataca aggttttta tcaagctgga taagagcatg      7800
atagtgggta gtgccatctt gatgaagctc agaagcaaca ccaaggaaga aaataagaaa      7860
aggtgtgagt ttctcccaga gaaactggaa taaatcatct ctttgagatg agcacttggg      7920
gtaggtaagg aaaacatatt tagattggag tctgaagttc ttgctagcag aaggcatgtt      7980
gttgtgactc cgaggggttg cctcaaactc tatcttataa ccggcgtgga ggcatggagg      8040
caagggcatt ttggtaattt aagtagttag tggaaaatga cgtcatttac ttaaagacga      8100
agtcttgcga caagggggc ccacgccgaa ttttaatatt accggcgtgg ccccaccta      8160 tcgcgagtgc tttagcacga gcggtccaga tttaaagtag aaaagttccc gcccactagg      8220
gttaaaggtg ttcacactat aaaagcatat acgatgtgat ggtatttgat ggagcgtata      8280
ttgtatcagg tatttccgtc ggatacgaat tattcgtacg gccggaccgg tcccctaggc      8340
cggccaattc gagatcggcc gcggctgagt ggctccttca atcgttgcgg ttctgtcagt      8400
tccaaacgta aaacggcttg tcccgcgtca tcggcggggg tcataacgtg actcccttaa      8460
ttctccgctc atgatcagat tgtcgtttcc cgccttcagt ttaaactatc agtgtttgac      8520
aggatatatt ggcgggtaaa cctaagagaa aagagcgttt attagaataa tcggatattt      8580
aaaagggcgt gaaaaggttt atccgttcgt ccatttgtat gtgcatgcca accacagggt      8640
tccccagatc tggcgccggc cagcgagacg agcaagattg ccgccgccc gaaacgatcc      8700 gacagcgcgc ccagcacagg tgcgcaggca aattgcacca acgcatacag cgccagcaga      8760
atgccatagt gggcggtgac gtcgttcgag tgaaccagat cgcgcaggag gcccggcagc      8820
accggcataa tcaggccgat gccgacagcg tcgagcgcga cagtgctcag aattacgatc      8880
aggggtatgt tgggtttcac gtctggcctc cggagactgt catacgcgta aaaaggccgc      8940
gttgctggcg ttttttccata ggctccgccc cctgacgag catcacaaaa atcgacgctc      9000
aagtcagagg tggcgaaacc cgacaggact ataaagatac caggcgtttc ccctggaag      9060 ctccctcgtg cgctctcctg ttccgaccct gccgcttacc ggatacctgt ccgcctttct      9120
```

```
cccttcggga agcgtggcgc tttctcatag ctcacgctgt aggtatctca gttcggtgta    9180
ggtcgttcgc tccaagctgg gctgtgtgca cgaaccccccc gttcagcccg accgctgcgc   9240
cttatccggt aactatcgtc ttgagtccaa cccggtaaga cacgacttat cgccactggc    9300
agcagccact ggtaacagga ttagcagagc gaggtatgta ggcggtgcta cagagttctt    9360
gaagtggtgg cctaactacg gctacactag aaggacagta tttggtatct gcgctctgct    9420
gaagccagtt accttcggaa aaagagttgg tagctcttga tccggcaaac aaaccaccgc    9480
tggtagcggt ggtttttttg tttgcaagca gcagattacg cgcagaaaaa aaggatctca    9540
agaagatcct ttgatctttt ctacgggtc tgacgctcag tggaacgaaa actcacgtta     9600
agggattttg gtcatgagat tatcaaaaag gatcttcacc tagatccttt taaattaaaa    9660
atgaagtttt aaatcaatct aaagtatata tgagtaaact tggtctgcag ttgccatgtt    9720
ttacggcagt gagagcagag atagcgctga tgtccggcgg tgcttttgcc gttacgcacc    9780
accccgtcag tagctgaaca ggagggacag ctgatagaca cagaagccac tggagcacct    9840
caaaaacacc atcatacact aaatcagtaa gttggcagca tcacccataa ttgtggtttc    9900
aaaatcggct ccgtcgatac tatgttatac gccaactttg aaaacaactt tgaaaaagct    9960
gttttctggt atttaaggtt ttagaatgca aggaacagtg aattggagtt cgtcttgtta   10020
taattagctt cttggggtat ctttaaatac tgtagaaaag aggaaggaaa taataaatgg   10080
ctaaaatgag aatatcaccg gaattgaaaa aactgatcga aaaataccgc tgcgtaaaag   10140
atacggaagg aatgtctcct gctaaggtat ataagctggt gggagaaaat gaaaacctat   10200
atttaaaaat gacggacagc cggtataaag ggaccaccta tgatgtggaa cgggaaaagg   10260
acatgatgct atggctggaa ggaaagctgc ctgttccaaa ggtcctgcac tttgaacggc   10320
atgatggctg gagcaatctg ctcatgagtg aggccgatgg cgtcctttgc tcggaagagt   10380
atgaagatga acaaagccct gaaaagatta tcgagctgta tgcggagtgc atcaggctct   10440
ttcactccat cgacatatcg gattgtccct atacgaatag cttagacagc cgcttagccg   10500
aattggatta cttactgaat aacgatctgg ccgatgtgga ttgcgaaaac tgggaagaag   10560
acactccatt taaagatccg cgcgagctgt atgattttt aaagacggaa aagcccgaag   10620
aggaacttgt cttttcccac ggcgacctgg gagacagcaa catctttgtg aaagatggca   10680
aagtaagtgg ctttattgat cttgggagaa gcggcagggc ggacaagtgg tatgacattg   10740
ccttctgcgt ccggtcgatc agggaggata tcggggaaga acagtatgtc gagctatttt   10800
ttgacttact ggggatcaag cctgattggg agaaaataaa atattatatt ttactggatg   10860 aattgttta gtacctagat gtggcgcaac gatgccggcg acaagcagga gcgcaccgac    10920
ttcttccgca tcaagtgttt tggctctcag gccgaggccc acggcaagta tttgggcaag   10980
gggtcgctgg tattcgtgca gggcaagatt cggaatacca agtacgagaa ggacggccag   11040
acggtctacg ggaccgactt cattgccgat aaggtggatt atctggacac caaggcacca   11100
ggcgggtcaa atcaggaata agggcacatt gccccggcgt gagtcggggc aatcccgcaa   11160
ggagggtgaa tgaatcggac gtttgaccgg aaggcataca ggcaagaact gatcgacgcg   11220
gggttttccg ccgaggatgc cgaaaccatc gcaagccgca ccgtcatgcg tgcgcccgc    11280 gaaaccttcc agtccgtcgg ctcgatggtc cagcaagcta cggccaagat cgagcgcgac   11340
agcgtgcaac tggctccccc tgccctgccc gcgccatcgg ccgccgtgga gcgttcgcgt   11400
cgtctcgaac aggaggcggc aggtttggcg aagtcgatga ccatcgacac gcgaggaact   11460
```

```
atgacgacca agaagcgaaa aaccgccggc gaggacctgg caaaacaggt cagcgaggcc    11520
aagcaggccg cgttgctgaa acacacgaag cagcagatca aggaaatgca gctttccttg    11580
ttcgatattg cgccgtggcc ggacacgatg cgagcgatgc caaacgacac ggcccgctct    11640
gccctgttca ccacgcgcaa caagaaaatc ccgcgcgagg cgctgcaaaa caaggtcatt    11700
ttccacgtca acaaggacgt gaagatcacc tacaccggcg tcgagctgcg ggccgacgat    11760
gacgaactgg tgtggcagca ggtgttggag tacgcgaagc gcaccccuat cggcgagccg    11820
atcaccttca cgttctacga gctttgccag gacctgggct ggtcgatcaa tggccggtat    11880
tacacgaagg ccgaggaatg cctgtcgcgc ctacaggcga cggcgatggg cttcacgtcc    11940
gaccgcgttg ggcacctgga atcggtgtcg ctgctgcacc gcttccgcgt cctggaccgt    12000
ggcaagaaaa cgtcccgttg ccaggtcctg atcgacgagg aaatcgtcgt gctgtttgct    12060
ggcgaccact acacgaaatt catatgggag aagtaccgca agctgtcgcc gacggcccga    12120
cggatgttcg actatttcag ctcgcaccgg gagccgtacc cgctcaagct ggaaaccttc    12180
cgcctcatgt gcggatcgga ttccacccgc gtgaagaagt ggcgcgagca ggtcggcgaa    12240
gcctgcgaag agttgcgagg cagcggcctg gtggaacacg cctgggtcaa tgatgacctg    12300
gtgcattgca aacgctaggg ccttgtgggg tcagttccgg ctgggggttc agcagccagc    12360
gctttactgg catttcagga acaagcgggc actgctcgac gcacttgctt cgctcagtat    12420
cgctcgggac gcacggcgcg ctctacgaac tgccgataaa cagaggatta aaattgacaa    12480
ttcaatggca aggactgcca gcgctgccat ttttggggtg aggccgttcg cggccgaggg    12540
gcgcagcccc tgggggatg ggaggcccgc gttagcgggc cggagggtt cgagaagggg    12600 gggcaccccc cttcggcgtg cgcggtcacg cgcacagggc gcagccctgg ttaaaaacaa    12660
ggtttataaa tattggttta aaagcaggtt aaaagacagg ttagcggtgg ccgaaaaacg    12720
ggcggaaacc cttgcaaatg ctggattttc tgcctgtgga cagcccctca aatgtcaata    12780
ggtgcgcccc tcatctgtca gcactctgcc cctcaagtgt caaggatcgc gcccctcatc    12840
tgtcagtagt cgcgcccctc aagtgtcaat accgcagggc acttatcccc aggcttgtcc    12900
acatcatctg tgggaaactc gcgtaaaatc aggcgttttc gccgatttgc gaggctggcc    12960
agctccacgt cgccggccga atcgagcct gcccctcatc tgtcaacgcc gcgccgggtg    13020
agtcggcccc tcaagtgtca acgtccgccc tcatctgtc agtgagggcc aagttttccg    13080
cgaggtatcc acaacgccgg cggccgcggt gtctcgcaca cggcttcgac ggcgtttctg    13140
gcgcgtttgc agggccatag acggccgcca gcccagcggc gagggcaacc agcccggtga    13200
gcgtcgcaaa ggcgctcggt cttgccttgc tcgtcgagat ctggggtcga tcagccgggg    13260
atgcatcagg ccgacagtcg gaacttcggg tccccgacct gtaccattcg gtgagcaatg    13320 gatagggggag ttgatatcgt caacgttcac ttctaaagaa atagcgccac tcagcttcct    13380
cagcggcttt atccagcgat ttcctattat gtcggcatag ttctcaagat cgacagcctg    13440
tcacggttaa gcgagaaatg aataagaagg ctgataattc ggatctctgc gagggagatg    13500
atatttgatc acaggcagca acgctctgtc atcgttacaa tcaacatgct accctccgcg    13560
agatcatccg tgtttcaaac ccggcagctt agttgccgtt cttccgaata gcatcggtaa    13620
catgagcaaa gtctgccgcc ttacaacggc tctcccgctg acgccgtccc ggactgatgg    13680
gctgcctgta tcgagtggtg atttgtgcc gagctgccgg tcggggagct gttggctggc    13740
tggtggcagg atatattgtg gtgtaaacaa attgacgctt agacaactta ataacacatt    13800
gcggacgttt ttaatgtact ggggtggttt ttcttttcac cagtgagacg ggcaacagct    13860
```

-continued

```
gattgccctt caccgcctgg ccctgagaga gttgcagcaa gcggtccacg ctggtttgcc    13920
ccagcaggcg aaaatcctgt ttgatggtgg ttccgaaatc ggcaaaatcc cttataaatc    13980
aaaagaatag cccgagatag ggttgagtgt tgttccagtt tggaacaaga gtccactatt    14040
aaagaacgtg gactccaacg tcaaagggcg aaaaaccgtc tatcagggcg atggcccact    14100
acgtgaacca tcacccaaat caagtttttt ggggtcgagg tgccgtaaag cactaaatcg    14160
gaaccctaaa gggagccccc gatttagagc ttgacgggga aagccggcga acgtggcgag    14220
aaaggaaggg aagaaagcga aaggagcggg cgccattcag gctgcgcaac tgttgggaag    14280
gg                                                                   14282
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His His His His His His Gly Ser
1               5

<210> SEQ ID NO 16
<211> LENGTH: 370
<212> TYPE: PRT
<213> ORGANISM: Clostridium perfringens

<400> SEQUENCE: 16

Trp Asp Gly Lys Ile Asp Gly Thr Gly Thr His Ala Met Ile Val Thr
1               5                   10                  15

Gln Gly Val Ser Ile Leu Glu Asn Asp Met Ser Lys Asn Glu Pro Glu
            20                  25                  30

Ser Val Arg Lys Asn Leu Glu Ile Leu Lys Asp Asn Met His Glu Leu
        35                  40                  45

Gln Leu Gly Ser Thr Tyr Pro Asp Tyr Asp Lys Asn Ala Tyr Asp Leu
    50                  55                  60

Tyr Gln Asp His Phe Trp Asp Pro Asp Thr Asn Asn Asn Phe Ser Lys
65                  70                  75                  80

Asp Asn Ser Trp Tyr Leu Ala Tyr Ser Ile Pro Asp Thr Gly Glu Ser
                85                  90                  95

Gln Ile Arg Lys Phe Ser Ala Leu Ala Arg Tyr Glu Trp Gln Arg Gly
            100                 105                 110

Asn Tyr Lys Gln Ala Thr Phe Tyr Leu Gly Glu Ala Met His Tyr Phe
        115                 120                 125

Gly Asp Ile Asp Thr Pro Tyr His Pro Ala Asn Val Thr Ala Val Asp
    130                 135                 140

Ser Ala Gly His Val Lys Phe Glu Thr Phe Ala Glu Glu Arg Lys Glu
145                 150                 155                 160

Gln Tyr Lys Ile Asn Thr Val Gly Cys Lys Thr Asn Glu Asp Phe Tyr
                165                 170                 175

Ala Asp Ile Leu Lys Asn Lys Asp Phe Asn Ala Trp Ser Lys Glu Tyr
            180                 185                 190

Ala Arg Gly Phe Ala Lys Thr Gly Lys Ser Ile Tyr Tyr Ser His Ala
        195                 200                 205

Ser Met Ser His Ser Trp Asp Asp Trp Asp Tyr Ala Ala Lys Val Thr

```
        210                 215                 220
Leu Ala Asn Ser Gln Lys Gly Thr Ala Gly Tyr Ile Tyr Arg Phe Leu
225                 230                 235                 240

His Asp Val Ser Glu Gly Asn Asp Pro Ser Val Gly Asn Asn Val Lys
                245                 250                 255

Glu Leu Val Ala Tyr Ile Ser Thr Ser Gly Glu Lys Asp Ala Gly Thr
            260                 265                 270

Asp Asp Tyr Met Tyr Phe Gly Ile Lys Thr Lys Asp Gly Lys Thr Gln
        275                 280                 285

Glu Trp Glu Met Asp Asn Pro Gly Asn Asp Phe Met Ala Gly Ser Lys
    290                 295                 300

Asp Thr Tyr Thr Phe Lys Leu Lys Asp Glu Asn Leu Lys Ile Asp Asp
305                 310                 315                 320

Ile Gln Asn Met Trp Ile Arg Lys Arg Lys Tyr Thr Ala Phe Pro Asp
                325                 330                 335

Ala Tyr Lys Pro Glu Asn Ile Lys Val Ile Ala Asn Gly Lys Val Val
            340                 345                 350

Val Asp Lys Asp Ile Asn Glu Trp Ile Ser Gly Asn Ser Thr Tyr Asn
        355                 360                 365

Ile Lys
    370

<210> SEQ ID NO 17
<211> LENGTH: 322
<212> TYPE: PRT
<213> ORGANISM: Clostridium perfringens

<400> SEQUENCE: 17

Met Lys Arg Leu Lys Ile Ile Ser Ile Thr Leu Val Leu Thr Ser Val
1               5                   10                  15

Ile Ser Thr Ser Leu Phe Ser Thr Gln Thr Gln Val Phe Ala Ser Glu
            20                  25                  30

Leu Asn Asp Ile Asn Lys Ile Glu Leu Lys Asn Leu Ser Gly Glu Ile
        35                  40                  45

Ile Lys Glu Asn Gly Lys Glu Ala Ile Lys Tyr Thr Ser Ser Asp Thr
    50                  55                  60

Ala Ser His Lys Gly Trp Lys Ala Thr Leu Ser Gly Thr Phe Ile Glu
65                  70                  75                  80

Asp Pro His Ser Asp Lys Lys Thr Ala Leu Leu Asn Leu Glu Gly Phe
                85                  90                  95

Ile Pro Ser Asp Lys Gln Ile Phe Gly Ser Lys Tyr Tyr Gly Lys Met
            100                 105                 110

Lys Trp Pro Glu Thr Tyr Arg Ile Asn Val Lys Ser Ala Asp Val Asn
        115                 120                 125

Asn Asn Ile Lys Ile Ala Asn Ser Ile Pro Lys Asn Thr Ile Asp Lys
    130                 135                 140

Lys Asp Val Ser Asn Ser Ile Gly Tyr Ser Ile Gly Gly Asn Ile Ser
145                 150                 155                 160

Val Glu Gly Lys Thr Ala Gly Ala Gly Ile Asn Ala Ser Tyr Asn Val
                165                 170                 175

Gln Asn Thr Ile Ser Tyr Glu Gln Pro Asp Phe Arg Thr Ile Gln Arg
            180                 185                 190

Lys Asp Asp Ala Asn Leu Ala Ser Trp Asp Ile Lys Phe Val Glu Thr
        195                 200                 205
```

-continued

```
Lys Asp Gly Tyr Asn Ile Asp Ser Tyr His Ala Ile Tyr Gly Asn Gln
    210             215             220

Leu Phe Met Lys Ser Arg Leu Tyr Asn Asn Gly Asp Lys Asn Phe Thr
225             230             235             240

Asp Asp Arg Asp Leu Ser Thr Leu Ile Ser Gly Gly Phe Ser Pro Asn
            245             250             255

Met Ala Leu Ala Leu Thr Ala Pro Lys Asn Ala Lys Glu Ser Val Ile
            260             265             270

Ile Val Glu Tyr Gln Arg Phe Asp Asn Asp Tyr Ile Leu Asn Trp Glu
        275             280             285

Thr Thr Gln Trp Arg Gly Thr Asn Lys Leu Ser Ser Thr Ser Glu Tyr
    290             295             300

Asn Glu Phe Met Phe Lys Ile Asn Trp Gln Asp His Lys Ile Glu Tyr
305             310             315             320

Tyr Leu
```